(12) United States Patent
Lipkens et al.

(10) Patent No.: US 11,085,035 B2
(45) Date of Patent: Aug. 10, 2021

(54) THERAPEUTIC CELL WASHING, CONCENTRATION, AND SEPARATION UTILIZING ACOUSTOPHORESIS

(71) Applicant: FloDesign Sonics, Inc., Wilbraham, MA (US)

(72) Inventors: Bart Lipkens, Bloomfield, CT (US); Jason Dionne, Simsbury, CT (US); Walter M. Presz, Jr., Wilbraham, MA (US); Brian Dutra, Fast Longmeadow, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 15/942,427

(22) Filed: Mar. 30, 2018

(65) Prior Publication Data

US 2018/0223273 A1    Aug. 9, 2018

Related U.S. Application Data

(63) Continuation-in-part of application No. 15/586,116, filed on May 3, 2017, now Pat. No. 10,640,760.

(60) Provisional application No. 62/330,947, filed on May 3, 2016, provisional application No. 62/359,182, filed on Jul. 6, 2016, provisional application No.
(Continued)

(51) Int. Cl.
| | | |
|---|---|---|
| *B06B 1/00* | (2006.01) | |
| *A61L 2/00* | (2006.01) | |
| *B08B 3/12* | (2006.01) | |
| *C12N 13/00* | (2006.01) | |
| *C12N 1/02* | (2006.01) | |
| *C12M 1/00* | (2006.01) | |

(52) U.S. Cl.
CPC ............. *C12N 13/00* (2013.01); *C12M 47/02* (2013.01); *C12M 47/04* (2013.01); *C12N 1/02* (2013.01)

(58) Field of Classification Search
CPC ...... B01D 43/00; B01D 21/283; C12N 13/00; B06B 1/0622; B01J 19/10; C02F 1/36
USPC .............................. 422/127–128, 292; 134/1
See application file for complete search history.

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| AU | 2002236405 | 9/2002 |
| CN | 103906496 A | 7/2014 |

(Continued)

OTHER PUBLICATIONS

Alvarez et al.; Shock Waves, vol. 17, No. 6, pp. 441-447, 2008.
(Continued)

*Primary Examiner* — Monzer R Chorbaji
(74) *Attorney, Agent, or Firm* — FloDesign Sonics, Inc.

(57) ABSTRACT

Multi-stage acoustophoretic devices for continuously separating a second fluid or a particulate from a host fluid are disclosed. Methods of operating the multi-stage acoustophoretic devices are also disclosed. The systems may include multiple acoustophoretic devices fluidly connected to one another in series, each acoustophoretic device comprising a flow chamber, an ultrasonic transducer capable of creating a multi-dimensional acoustic standing wave, and a reflector. The systems can further include pumps and flowmeters.

22 Claims, 29 Drawing Sheets

Related U.S. Application Data

62/374,910, filed on Aug. 15, 2016, provisional application No. 62/479,309, filed on Mar. 30, 2017.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |

(56) References Cited

U.S. PATENT DOCUMENTS

| | | |
|---|---|---|
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliaysky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,902,974 B2 | 2/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,947,431 B2 | 4/2018 | El-Zahab et al. |
| 9,974,898 B2 | 5/2018 | Spain et al. |
| 9,983,459 B2 | 5/2018 | Arnold |
| 10,006,052 B2 | 6/2018 | Jarjour |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0316411 A1 | 11/2013 | Schultz |

(56) References Cited

U.S. PATENT DOCUMENTS

| | | |
|---|---|---|
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0056715 A1* | 2/2015 | Laugharn, Jr. ....... G01N 1/4044 436/175 |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galetto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |

(56) References Cited

U.S. PATENT DOCUMENTS

| | | | |
|---|---|---|---|
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0010758 A1 | 5/2018 | Vincent et al. |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0143138 A1 | 5/2018 | Shreve et al. |
| 2018/0143167 A1 | 5/2018 | Mziray et al. |
| 2018/0147245 A1 | 5/2018 | O'Shea et al. |
| 2018/0147576 A1 | 5/2018 | Lavieu et al. |
| 2018/0148740 A1 | 5/2018 | Conway et al. |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha |

FOREIGN PATENT DOCUMENTS

| | | | | |
|---|---|---|---|---|
| CN | 105 087 788 A | 11/2015 | | |
| CN | 104722106 B | 4/2016 | | |
| DE | 30 27 433 A1 | 2/1982 | | |
| DE | 32 18 488 A1 | 11/1983 | | |
| DE | 196 48 519 A1 | 6/1998 | | |
| DE | 103 19 467 B3 | 7/2004 | | |
| DE | 10 2008 006 501 A1 | 9/2008 | | |
| DE | 10 2014 206 823 A1 | 10/2015 | | |
| EP | 0 292 470 B1 | 11/1988 | | |
| EP | 0 167 406 B1 | 7/1991 | | |
| EP | 0 641 606 | 3/1995 | | |
| EP | 1 175 931 A1 | 1/2002 | | |
| EP | 1 254 669 B1 | 11/2002 | | |
| EP | 1 308 724 A2 | 5/2003 | | |
| EP | 2 209 545 | 7/2010 | | |
| EP | 270152 A1 | 1/2018 | | |
| EP | 2419511 | 1/2018 | | |
| EP | 3068888 | 1/2018 | | |
| EP | 3257600 | 1/2018 | | |
| EP | 3274453 | 1/2018 | | |
| EP | 3274454 | 1/2018 | | |
| EP | 3275894 | 1/2018 | | |
| EP | 278108 | 2/2018 | | |
| EP | 3279315 | 2/2018 | | |
| EP | 3286214 | 2/2018 | | |
| EP | 2289535 | 3/2018 | | |
| EP | 2545068 | 3/2018 | | |
| EP | 2675540 | 3/2018 | | |
| EP | 2750683 | 3/2018 | | |
| EP | 2796102 | 3/2018 | | |
| EP | 3066201 | 3/2018 | | |
| EP | 3066998 | 3/2018 | | |
| EP | 3107552 | 3/2018 | | |
| EP | 3288660 | 3/2018 | | |
| EP | 3288683 | 3/2018 | | |
| EP | 3289362 | 3/2018 | | |
| EP | 3291842 | 3/2018 | | |
| EP | 3291852 | 3/2018 | | |
| EP | 3292142 | 3/2018 | | |
| EP | 3292195 | 3/2018 | | |
| EP | 3292515 | 3/2018 | | |
| EP | 3294343 | 3/2018 | | |
| EP | 3294764 | 3/2018 | | |
| EP | 3294857 | 3/2018 | | |
| EP | 3294871 | 3/2018 | | |
| EP | 3294888 | 3/2018 | | |
| EP | 3294896 | 3/2018 | | |
| EP | 3296302 | 3/2018 | | |
| EP | 3297740 | 3/2018 | | |
| EP | 3298046 | 3/2018 | | |
| EP | 3164488 | 4/2018 | | |
| EP | 3301115 | 4/2018 | | |
| EP | 3302783 | 4/2018 | | |
| EP | 3302789 | 4/2018 | | |
| EP | 3303558 | 4/2018 | | |
| EP | 3306310 | 4/2018 | | |
| EP | 2675901 | 5/2018 | | |
| EP | 2956772 | 5/2018 | | |
| EP | 3323444 | 5/2018 | | |
| EP | 3324996 | 5/2018 | | |
| EP | 3327127 | 5/2018 | | |
| EP | 3337819 | 6/2018 | | |
| GB | 2 420 510 A | 5/2006 | | |
| JP | 9-136090 | 5/1997 | | |
| KR | 1442486 | 9/2014 | | |
| RU | 2037327 C1 | 6/1995 | | |
| RU | 2085933 | 7/1997 | | |
| SU | 629496 | 10/1978 | | |
| WO | WO 1987/07178 A1 | 12/1987 | | |
| WO | WO 89/11899 A1 | 12/1989 | | |
| WO | WO 90/05008 | 3/1990 | | |
| WO | WO 95/01214 A1 | 1/1995 | | |
| WO | WO 97/34643 | 9/1997 | | |
| WO | WO 1998/017373 | 4/1998 | | |
| WO | WO 98/50133 A1 | 11/1998 | | |
| WO | WO 00/41794 | 7/2000 | | |
| WO | WO 02/072234 A1 | 9/2002 | | |
| WO | WO 02/072236 A1 | 9/2002 | | |
| WO | WO 03/089567 | 10/2003 | | |
| WO | WO 2004/079716 A1 | 9/2004 | | |
| WO | WO 2009/063198 | 5/2009 | | |
| WO | WO-2009063198 A2 * | 5/2009 | ......... | C12N 15/1003 |
| WO | WO 2009/111276 A1 | 9/2009 | | |
| WO | WO 2009/144709 A1 | 12/2009 | | |
| WO | WO 2010/024753 A1 | 4/2010 | | |
| WO | WO 2010/040394 A1 | 4/2010 | | |
| WO | WO 2011/023949 A2 | 3/2011 | | |
| WO | WO 2011/025890 A1 | 3/2011 | | |
| WO | WO 2011/027146 A2 | 3/2011 | | |
| WO | WO 2011/131947 A2 | 10/2011 | | |
| WO | WO 2011/161463 A2 | 12/2011 | | |
| WO | WO 2013/043044 A1 | 3/2013 | | |
| WO | WO 2013/043297 A1 | 3/2013 | | |
| WO | WO 2013/049623 A1 | 4/2013 | | |
| WO | WO 2013/055517 A1 | 4/2013 | | |
| WO | WO-2013049623 A1 * | 4/2013 | ................ | A61J 3/00 |
| WO | WO 2013/138797 A1 | 9/2013 | | |
| WO | WO 2013/148376 | 10/2013 | | |
| WO | WO 2013/159014 A1 | 10/2013 | | |
| WO | WO 2014/014941 A1 | 1/2014 | | |
| WO | WO 2014/029505 | 2/2014 | | |
| WO | WO 2014/035457 | 3/2014 | | |
| WO | WO 2014/046605 A1 | 3/2014 | | |
| WO | WO 2014/055219 A2 | 4/2014 | | |
| WO | WO 2014/124306 A1 | 8/2014 | | |
| WO | WO 2014/153651 | 10/2014 | | |
| WO | WO 2014/165177 | 10/2014 | | |
| WO | WO 2015/006730 | 1/2015 | | |
| WO | WO 2015/102528 | 7/2015 | | |
| WO | WO 2016/004398 A2 | 1/2016 | | |
| WO | WO 2016/124542 | 8/2016 | | |
| WO | WO 2016/176663 | 11/2016 | | |

(56) References Cited

FOREIGN PATENT DOCUMENTS

| | | |
|---|---|---|
| WO | WO 2016/209082 | 12/2016 |
| WO | WO 2017/011519 | 1/2017 |
| WO | WO 2017/021543 | 2/2017 |
| WO | WO 2017/041102 | 3/2017 |
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO 2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018058275 | 5/2018 |
| WO | WO 2018081476 | 5/2018 |
| WO | WO 2018091879 | 5/2018 |
| WO | WO2018094244 | 5/2018 |
| WO | WO 20180814701 | 5/2018 |
| WO | WO 2018098671 | 6/2018 |
| WO | WO 2018102752 | 6/2018 |
| WO | WO 2018106163 | 6/2018 |
| WO | WO 2018112145 | 6/2018 |
| WO | WO 2018112335 | 6/2018 |

OTHER PUBLICATIONS

Augustsson et al., Acoustophoretic microfluidic chip for sequential elution of surface bound molecules from beads or cells, Biomicrofluidics, Sep. 2012, 6(3):34115.
Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
PHYS. ORG. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer Aided Design; vol. 30; No. 11; 1998.

(56) References Cited

OTHER PUBLICATIONS

Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index. html>.
International Search Report and Written Opinion for International Application No. PCT/US2017/031425 dated Oct. 23, 2017.

\* cited by examiner

THERAPEUTIC CELL WASHING, CONCENTRATION, AND SEPARATION UTILIZING ACOUSTOPHORESIS

CROSS-REFERENCE TO RELATED APPLICATIONS

This application is a continuation-in-part of U.S. patent application Ser. No. 15/586,116, filed on May 3, 2017, which claims priority to U.S. Provisional Patent Application Ser. No. 62/330,947, filed on May 3, 2016, and to U.S. Provisional Patent Application Ser. No. 62/359,182, filed on Jul. 6, 2016, and to U.S. Provisional Patent Application Ser. No. 62/374,910, filed on Aug. 15, 2016. This application also claims the benefit of U.S. Provisional Patent Application Ser. No. 62/479,309, filed on Mar. 30, 2017. The disclosures of these applications are hereby fully incorporated herein by reference in their entirety.

BACKGROUND

Concentrating therapeutic cells and transferring them from one solution into another (usually referred to as washing) are two processes involved at multiple stages of production and use of the cells. The washing and separation of materials in cellular processing is an important part of the overall efficacy of the cell therapy of choice. In particular, therapeutic cells may originally be suspended in a growth serum or in preservative materials like dimethyl sulfoxide (DMSO). Separating the cells from these fluids so the cells can be further processed is important in the overall therapeutic process of using such cellular materials. In one example, the cells are typically recovered from a bioreactor, concentrated, and transferred from culture media into an electroporation buffer prior to transduction, such as in manufacturing CAR-T cells. After expansion of cells at the final manufacturing step, they are concentrated and transferred into an appropriate solvent depending on the desired application.

Therapeutic cells are stored in specialized media to prolong the viability of these cells either through refrigeration and or freezing processes. Such specialized media may not be compatible when the therapeutic cells are introduced into a patient. It may thus be helpful to both wash and concentrate the therapeutic cells in a buffer or wash media that is biocompatible with both the therapeutic cells and with the patient. These washing and concentration processes conventionally involve the use of centrifugation and physical filtration. The washing step may be repeated a number of times. For example, the specialized media (which can be pyrogenic or otherwise harmful) may be fully removed with multiple wash steps, and the cells may be suspended in a new buffer or wash solution. During this washing process, many of the cells are degraded or destroyed through the centrifugation and physical filtration processes. Moreover, the filtration process can be rather inefficient and may entail a non-sterile intrusion into the environment for batch processing, whereby the cell culture is exposed to possible pathogens or outside cellular influences that would be harmful to the target cell culture. Further yet, with these physical filtration processes, biological waste is generated through the use of multiple physical filters which may incur additional steps for proper disposal. The cost and timeliness of this process is also not conducive to a fast or low-cost process of preparing the cells for introduction to the patient.

BRIEF SUMMARY

The present disclosure provides methods and systems for replacing or augmenting conventional centrifugation and physical filtration processes along with the multiple washing steps with a simpler, lower cost, and more friendly process for particles such as therapeutic cells. The methods/processes can be performed in a sterile environment and in a continuous form.

Disclosed herein are methods of washing particles, which may be cells. In some example methods, an initial mixture of a first media and the particles is fed to a flow chamber of an acoustophoretic device. The first media may contain preservatives such as dimethyl sulfoxide (DMSO) which are undesirable for future applications/uses of the particles. The acoustophoretic device has at least one ultrasonic transducer that includes a piezoelectric material and is configured to be driven to create a multi-dimensional acoustic standing wave in the flow chamber. At least a portion of the particles are trapped in the multi-dimensional acoustic standing wave. A second media is flowed through the flow chamber to wash out the first media while the particles are retained in the multidimensional acoustic standing wave. The particles may thus experience a media exchange, where the first media is exchanged for the second media.

In some examples, the volume of the second media used to perform the wash process may be equivalent to a volume of the flow chamber. In some examples, the volume of the second media used to perform the wash process may be multiples of or portions of the volume of the flow chamber. The second media can be a biocompatible wash or a buffer solution.

The particles may be cells. The cells may be Chinese hamster ovary (CHO) cells, NS0 hybridoma cells, baby hamster kidney (BHK) cells, human cells, regulatory T-cells, Jurkat T-cells, CAR-T cells, B cells, or NK cells, peripheral blood mononuclear cells (PBMCs), algae, plant cells, bacteria, or viruses. The cells may be attached to microcarriers.

Sometimes, the piezoelectric material of the at least one ultrasonic transducer is in the form of a piezoelectric array formed from a plurality of piezoelectric elements. Each piezoelectric element can be physically separated from surrounding piezoelectric elements by a potting material. The piezoelectric array can be present on a single crystal, with one or more channels separating the piezoelectric elements from each other. Each piezoelectric element can be individually connected to its own pair of electrodes. The piezoelectric elements can be operated in phase with each other, or operated out of phase with each other. The acoustophoretic device may further comprise a cooling unit for cooling the at least one ultrasonic transducer.

In various embodiments, the initial mixture may have a density of about 0.5 million particles/mL to about 5 million particles/mL. The concentrated volume can be 25 to about 50 times less than a volume of the initial mixture. The concentrated volume may have a particle density of 25 to about 50 times greater than a particle density of the initial mixture.

Also disclosed in various embodiments are methods of recovering greater than 90% of cells from a cell culture. An initial mixture of a first media and the cell culture is fed through a flow chamber of an acoustophoretic device, the acoustophoretic device comprising at least one ultrasonic transducer including a piezoelectric material that is configured to be driven to create a multi-dimensional acoustic standing wave in the flow chamber. The at least one ultrasonic transducer is driven to create a multi-dimensional acoustic standing wave in the flow chamber, and thus to concentrate the cell culture within the acoustic standing wave. The initial mixture has an initial cell density of about 0.5 million cells/mL to about 5 million cells/mL, and the concentrated cell culture has a cell density at least 25 times greater than the initial cell density.

In some embodiments, the concentrated cell culture has a cell density of 25 to about 50 times greater than the initial cell density. In other embodiments, a volume of the concentrated cell culture is 25 to about 50 times less than a volume of the initial mixture. The concentrated cell culture can be obtained in about 35 minutes or less.

Also disclosed are acoustophoretic devices, comprising: a flow chamber having a fluid inlet, a first outlet, and a second outlet; at least one ultrasonic transducer proximate a first wall of the flow chamber, at least one ultrasonic transducer including a piezoelectric material that is adapted to be driven to create a multi-dimensional acoustic standing wave; a reflector on a second wall of the flow chamber opposite the at least one ultrasonic transducer; and a thermoelectric generator located between the at least one ultrasonic transducer and the first wall of the flow chamber.

The acoustophoretic device may have a concentrated volume of about 25 mL to about 75 mL. The acoustophoretic device may have a cell capacity of about 4 billion to about 40 billion cells. Various lines can connect the acoustophoretic device to containers that provide or receive various materials to/from the acoustophoretic device.

These and other non-limiting characteristics are more particularly described below.

BRIEF DESCRIPTION OF THE DRAWINGS

The following is a brief description of the drawings, which are presented for the purposes of illustrating the example embodiments disclosed herein and not for the purposes of limiting the same.

FIG. 22 shows a microscopic image of the microcarriers with T attached cells in the feed and during the three wash passes, and the concentration of separated microcarriers and T cells in the permeate.

DETAILED DESCRIPTION

Figure 1:
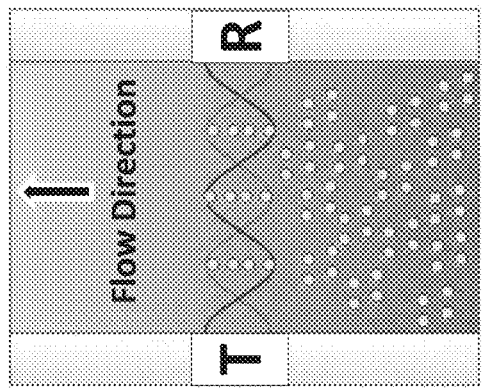
FIG. 1 illustrates an example acoustophoresis process using a transducer and reflector to create an acoustic standing wave for trapping particles and separating them from a fluid by enhanced gravitational settling.
Figure 1:
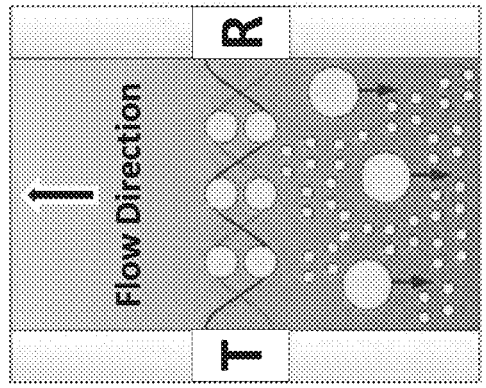
Figure 1:
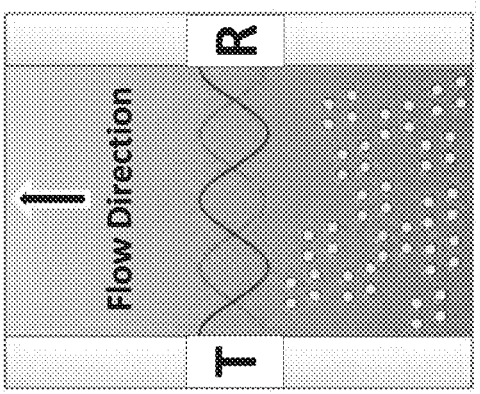
Figure 1:
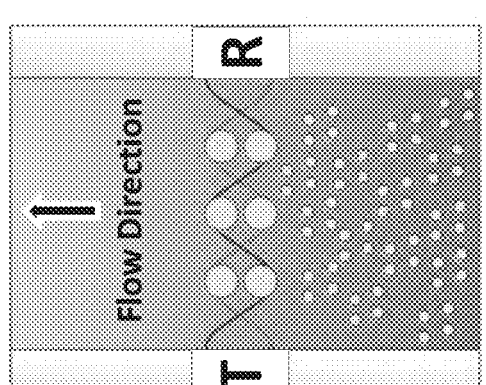

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, e.g. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, e.g. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, e.g. ground level. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least 1 and less than 10.

The acoustophoretic technology of the present disclosure employs acoustic standing waves to concentrate, wash, and/or separate materials (such as particles or a secondary fluid) in a primary or host fluid. In particular, as shown in the upper left image (A) of FIG. 1, an ultrasonic transducer T creates an acoustic wave in the fluid, which interacts with a reflector R positioned across from the ultrasonic transducer to create an acoustic standing wave. Although a reflector R is illustrated in FIG. 1, another transducer may be used to reflect and/or generate acoustic energy to form the acoustic standing wave.

As shown in the upper right image (B) of FIG. 1, as the host fluid and material entrained in the host fluid flows upwards through the acoustic standing wave, the acoustic standing wave(s) traps (retains or holds) the material (e.g., secondary phase materials, including fluids and/or particles). The scattering of the acoustic field off the material results in a three-dimensional acoustic radiation force, which acts as a three-dimensional trapping field.

The three-dimensional acoustic radiation force generated in conjunction with an ultrasonic standing wave is referred to in the present disclosure as a three-dimensional or multi-dimensional standing wave. The acoustic radiation force is proportional to the particle volume (e.g. the cube of the radius) of the material when the particle is small relative to the wavelength. The acoustic radiation force is proportional to frequency and the acoustic contrast factor. The acoustic radiation force scales with acoustic energy (e.g. the square of the acoustic pressure amplitude). For harmonic excitation, the sinusoidal spatial variation of the force drives the particles to the stable positions within the standing waves. When the acoustic radiation force exerted on the particles is stronger than the combined effect of fluid drag force and buoyancy and gravitational force, the particle can be trapped within the acoustic standing wave field, as shown in the upper right image (B) of FIG. 1.

As can be seen in the lower left image (C) of FIG. 1, this trapping results in coalescing, clumping, aggregating, agglomerating, and/or clustering of the trapped particles. Additionally, secondary inter-particle forces, such as Bjerkness forces, aid in particle agglomeration.

As the particles continue to coalesce, clump, aggregate, agglomerate, and/or cluster the particles can grow to a certain size at which gravitational forces on the particle cluster overcome the acoustic radiation force. At such size, the particle cluster can fall out of the acoustic standing wave, as shown in the lower right image (D) of FIG. 1.

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. A planar or one-dimensional acoustic standing wave may provide acoustic forces in the axial or wave propagation direction. The lateral force in planar or one-dimensional acoustic wave generation may be two orders of magnitude smaller than the axial force. The multi-dimensional acoustic standing wave may provide a lateral force that is significantly greater than that of the planar acoustic standing wave. For example, the lateral force may be of the same order of magnitude as the axial force in the multi-dimensional acoustic standing wave.

The acoustic standing waves of the present disclosure can be used to trap particles (e.g. therapeutic cells such as T cells, B cells, NK cells) suspended in a first media in the standing wave. The first media can then be replaced with a second media (e.g., a biocompatible wash or buffer solution). Put another way, the host fluid of the particles can be replaced. Prior to replacing the first media with the second media, acoustophoresis can be used to perform a diafiltration process, as shown in FIG. 2.

Figure 2:
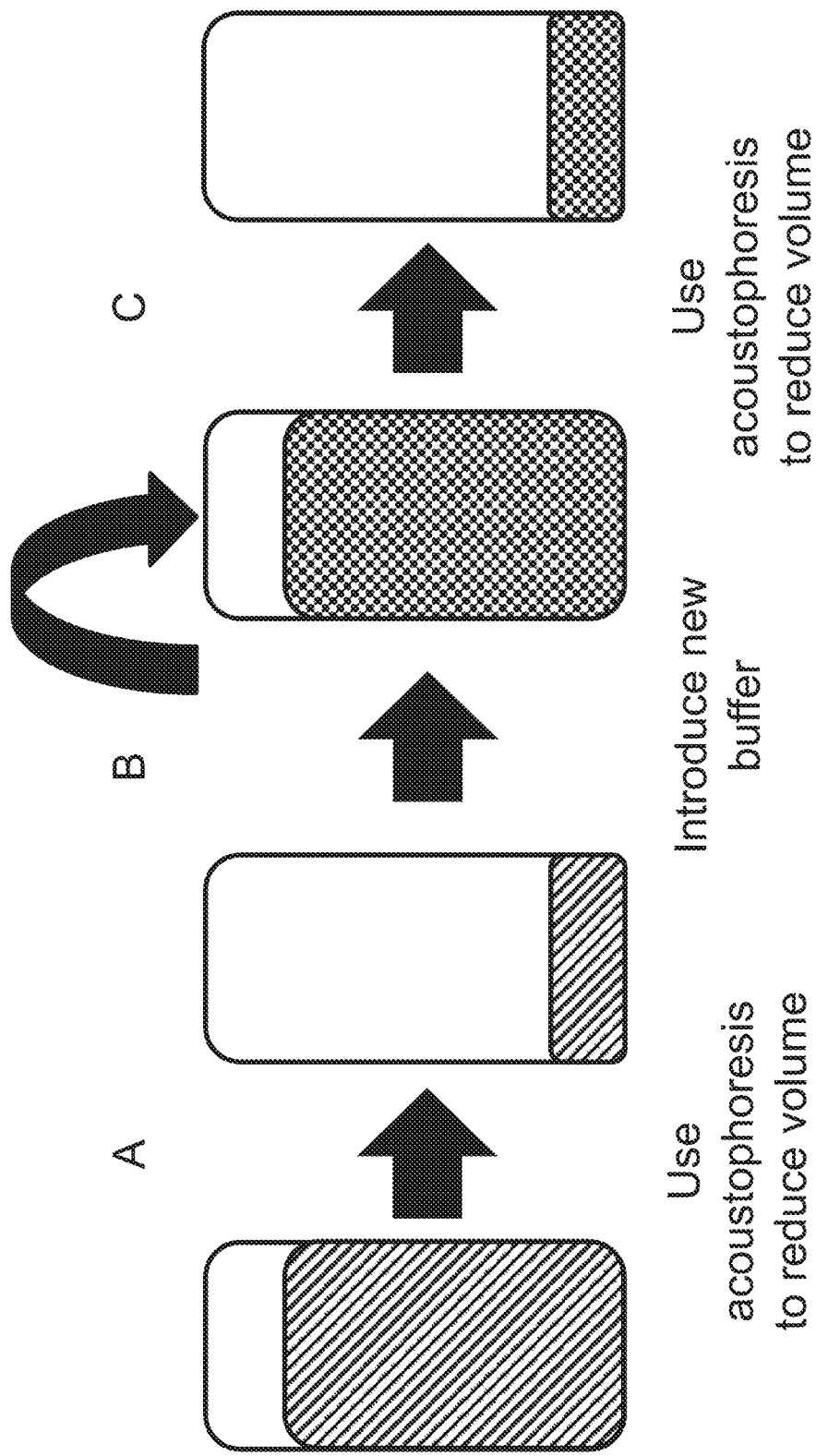
FIG. 2 illustrates an example cell concentration and washing process ("diafiltration") according to the present disclosure using acoustophoresis.

In FIG. 2, starting with an initial mixture that has a low cell density of, for example, less than $1 \times 10^6$ cells/mL, acoustophoresis can be used to reduce the volume of the initial mixture, for example by at least 10×, including 20× and up to 100× or more. The cell concentration may be increased by at least 10×, including 20× and up to 100× or more. This initial reduction process is the first volume reduction step (A). Next, the second media (e.g., a biocompatible wash or buffer solution) can be introduced to at least partially displace the first media, as indicated in step (B). Next, the new mixture of the cells and second media can be subjected to an acoustophoretic volume reduction step (C). This series of operations is referred to as a "diafiltration" process.

Figure 3:
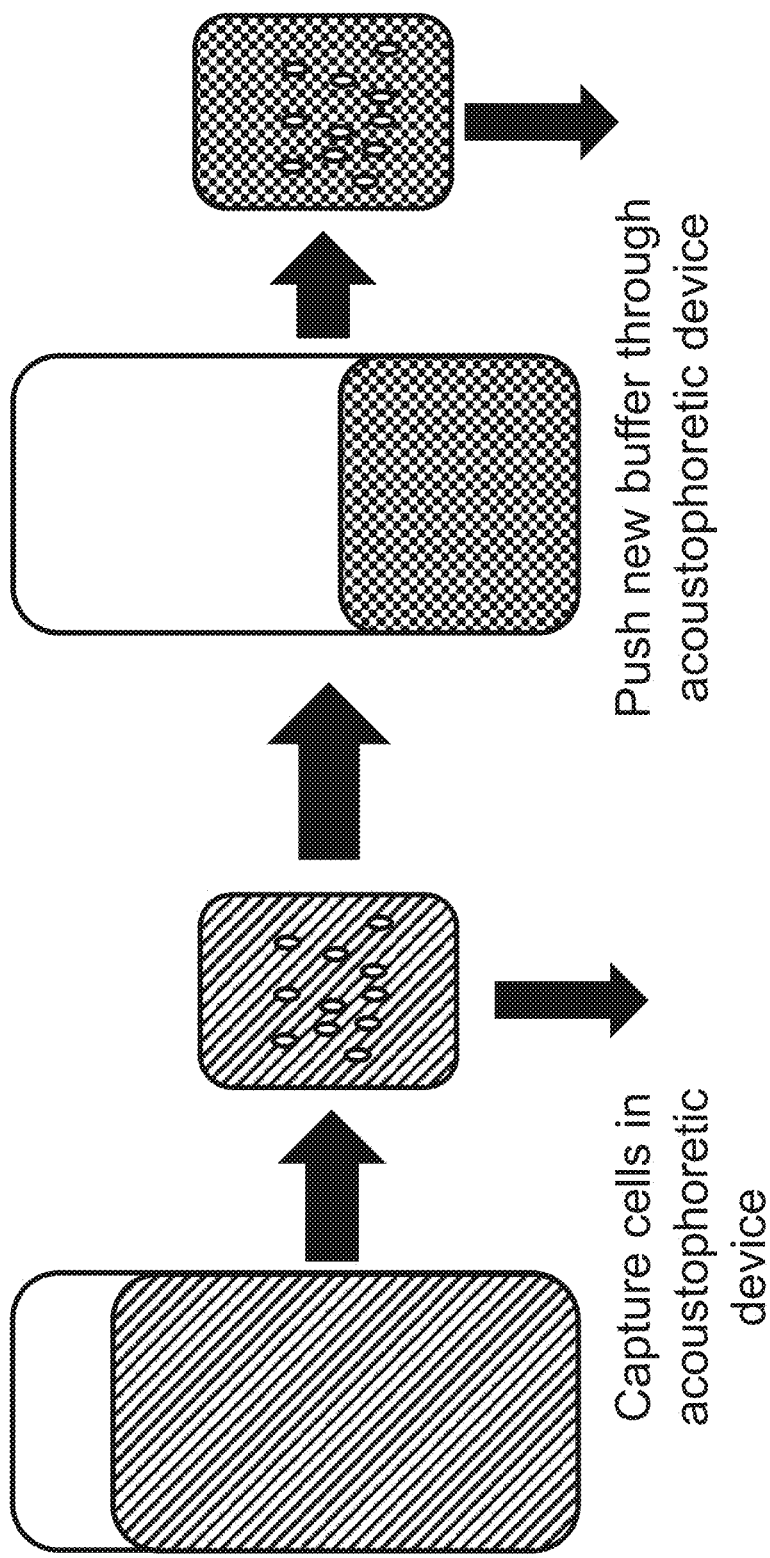
FIG. 3 illustrates another example cell concentration and washing process (push through) according to the present disclosure using acoustophoresis.

FIG. 3 illustrates a single-step, push-through process in which particles/cells are trapped in the acoustic standing wave and held in the acoustophoretic device. The second media (e.g., a biocompatible wash or buffer solution) is then flowed into the acoustophoretic device to effectively "wash out" the first media. With the push-through process, more than 90%, including up to 99% or more, of the first media can be removed from the particles/cells. The push-through process can be employed as a continuous, single-use process that uses less buffer solution and less time than the diafiltration process of FIG. 2.

Figure 4:
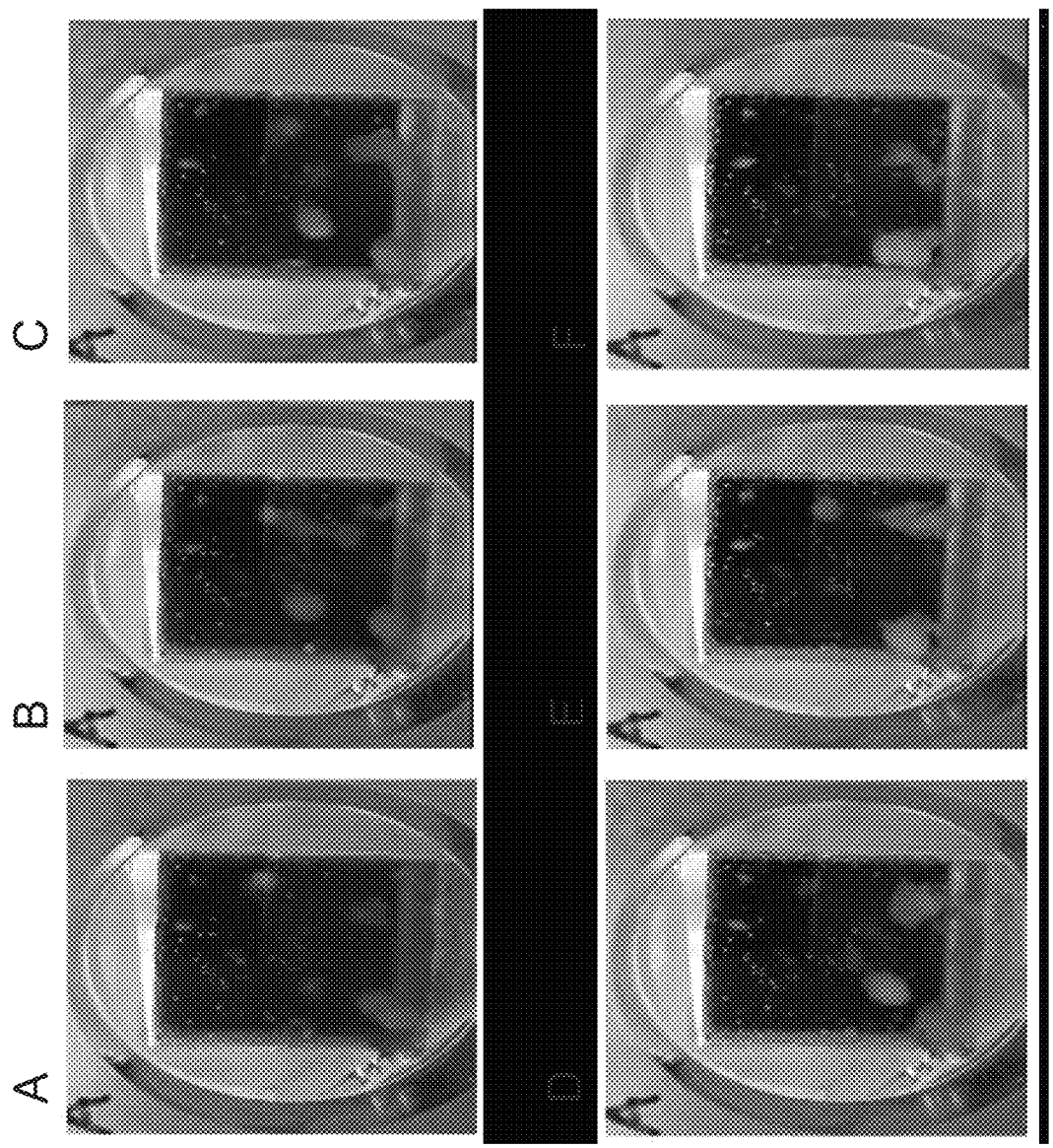
FIG. 4 shows six photographs that, from left to right and top to bottom, show the progression of cells being trapped in an acoustophoretic device before a second media mixture (dyed blue) is flowed into the device and gradually replaces the first media (dyed red).

FIG. 4 shows six photographs that, from left to right and top to bottom, show the progression of cells being trapped in an acoustophoretic device before a second media mixture (dyed blue) is flowed into the device and gradually replaces the first media (dyed red). In FIG. 4, a 150 mL feed volume was used with 80 mL of electroporation media wash for the second media. The concentrate was drawn off at a flow rate of 10 mL/minute. As can be seen in these pictures, over time the first media is replaced with the second media.

Figure 5:
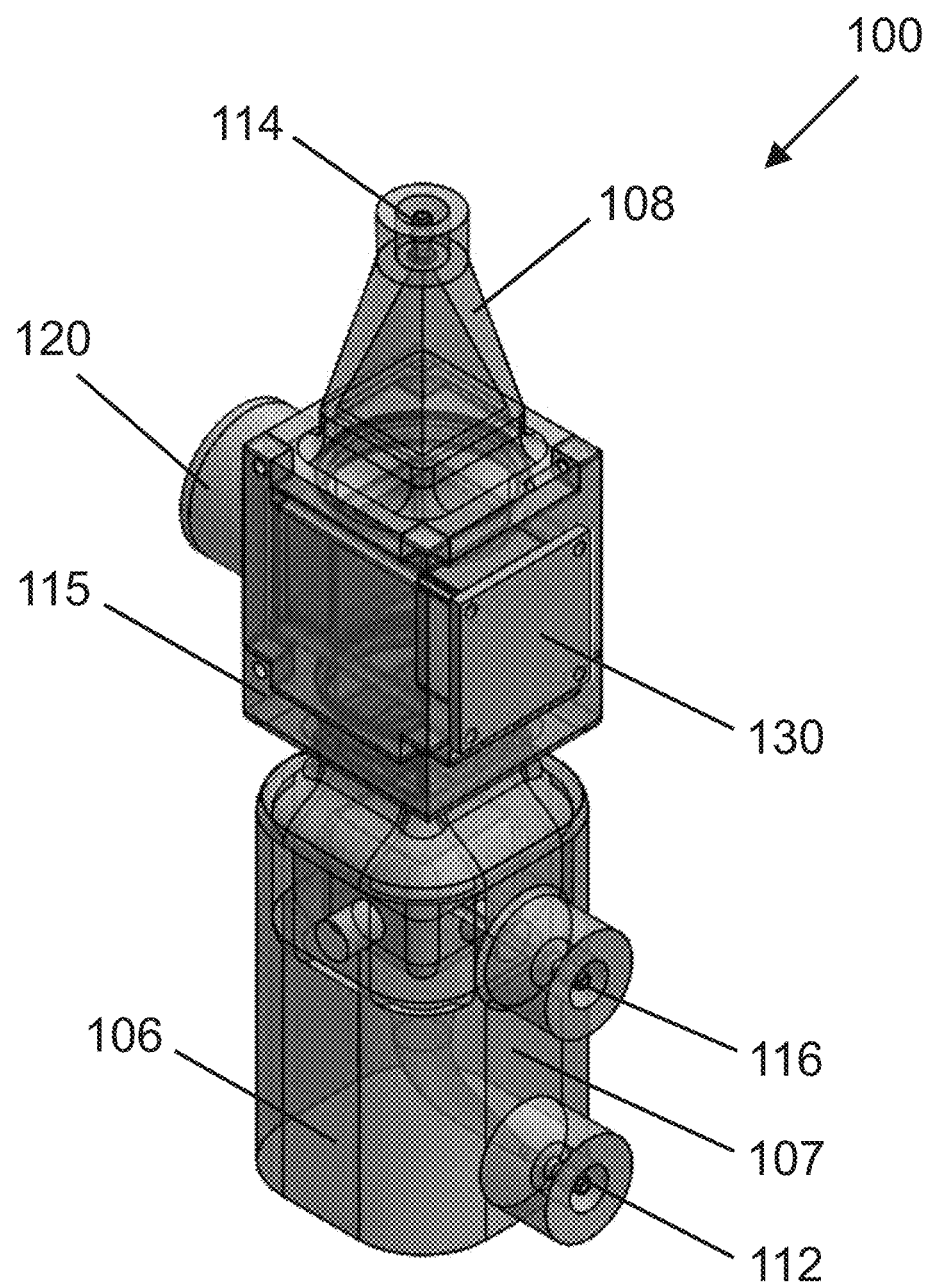
FIG. 5 is a perspective view of an example acoustophoretic device according to the present disclosure.
Figure 6:
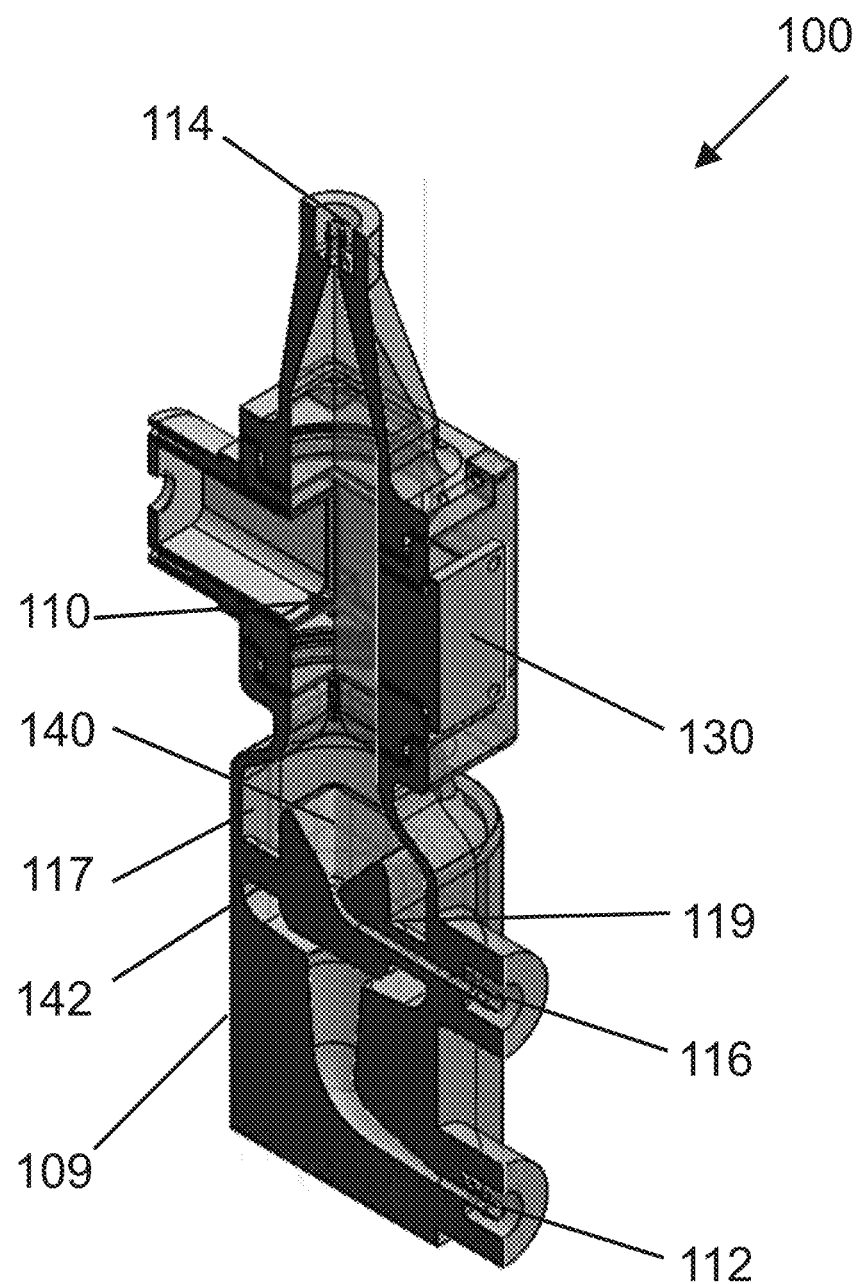
FIG. 6 is a cross-sectional illustration of the acoustophoretic device of FIG. 5.

With reference now to FIG. 5 and FIG. 6, a first example embodiment of an acoustophoretic device 100 for separation of particles/cells from fluid is depicted. The acoustophoretic device 100 includes a flow chamber 110 having at least one inlet and at least one outlet. In this embodiment, the flow chamber 110 includes inlet 112, permeate outlet 114, concentrate outlet 116, an ultrasonic transducer 120, and a reflector 130. The inlet 112 can, in certain embodiments, serve the dual function of introducing the cells surrounded by the first media into the flow chamber 110 in addition to introducing the second media into the flow chamber 110. Alternatively, separate inlets can be used for introducing the first and second media.

The flow chamber 110 is the region of the device 100 through which is flowed the cells surrounded by the first media. In this embodiment, the flow chamber 110 is defined by inlet 112, permeate outlet 114, and concentrate outlet 116. The flow chamber 110 is further defined by a sidewall 115 to which the ultrasonic transducer 120 and the reflector 130 are coupled. As seen here, the sidewall is shaped so that the ultrasonic transducer and reflector are located on opposite sides thereof.

Inlet 112 is located at a first end 106 of the flow chamber 110. In particular embodiments, the ingress of material through the inlet 112 can be configured to occur toward the bottom end of the inlet 112, such that the inflow of fluid into the flow chamber 110 occurs closer to the bottom end of the flow chamber 110 than the top end thereof.

As depicted in FIG. 5 and FIG. 6, the inlet 112 is located along a first side 107 of the device 100. The first side 107 of the device also houses the reflector 130, while a second side 109 of the device, opposite the first side thereof, houses the ultrasonic transducer 120. The inlet 112 could alternatively be located along the second side 109 of the device (e.g., on the same side as the ultrasonic transducer) or on another side of the device.

In the embodiment depicted in FIG. 5, the permeate outlet 114 is located at a second end 108 of the flow chamber 100. The permeate outlet 114 is generally used to recover the first media and residual cells from the flow chamber 110. In comparison, the concentrate outlet 116 is located between the inlet 112 and the permeate outlet 114, below the ultrasonic transducer 120 and the reflector 130. The concentrate outlet 116 is generally configured to recover the cells from the flow chamber 110. In certain embodiments, however, it may be desired to recover other material (e.g., microcarriers) from the device, in which case the microcarriers can be recovered by the concentrate outlet and the cells can be recovered via the permeate outlet along with the media). As seen here, the permeate outlet 114 is generally located above the ultrasonic transducer 120 and the reflector 130, while and the concentrate outlet 116 is generally located below the ultrasonic transducer 120 and the reflector 130.

In the embodiment depicted in FIG. 5 and FIG. 6, the device 100 is vertically oriented, such that the first end 106 of the device is the bottom end thereof and the second end 108 of the device is the top end thereof. In this way, the cells surrounded by the first media is introduced at the bottom end of the device 100 and flows vertically upwards through the flow chamber from the inlet 112 toward the permeate outlet 114.

As can be best seen in FIG. 6, the device 100 also includes a collector 140. The collector 140 is located in the flow chamber 110 between the inlet 112 and the ultrasonic transducer 120 and the reflector 130. The collector 140 is located above the concentrate outlet 116 and, in particular, is defined by angled walls 142 that lead to the concentrate outlet 116. Put another way, the collector 140 leads into a common well defined by angled walls 142 that taper downwards in cross-sectional area (i.e. larger area to smaller area) to a vertex at the bottom of the collector, which is fluidically connected to and drains off one side into the concentrate outlet 116 via flowpath 119. In this way, the multi-dimensional acoustic standing wave can direct the concentrated cells to the collector 140 for collection and removal from the flow chamber 110 via the concentrate outlet 116. An annular plenum 117 surrounds the collector 140, permitting the mixture of host fluid/cells to flow from the inlet 112 around the collector 140 into the flow chamber 110.

In some embodiments, the collector leads to a collection container that is filled with the second media. In this way, the second media is not flowed through the flow chamber of the device. Instead, as the cells are trapped in the acoustic standing wave and form clusters that grow to a critical size and subsequently fall out of the multi-dimensional acoustic standing wave, the cell clusters fall into the collector and are led to the collection container. The collection container can be separable from the rest of the device.

As seen here, preferably, fluid flows through the device upwards. The cells surrounded by the first media enters the device through inlet 112 at a bottom end of the device and then makes a sharp turn to flow upwards. This change in direction desirably reduces turbulence, producing near plug flow upwards through the device. Flow continues upwards through the annular plenum 117 and up into the flow chamber 110. There, the cells encounter the multi-dimensional acoustic standing wave(s), which traps the cells, as explained herein. Concentration of the cells occurs within the acoustic standing wave(s), which can also cause coalescence, clumping, aggregation, agglomeration and/or clustering of the cells.

As the cells are concentrated, they eventually overcome the combined effect of the fluid flow drag forces and acoustic radiation force, and they fall downwards into collector 140. They can then be flowed through flowpath 119 and collected at concentrate outlet 116. A much higher number of cells is obtained in a smaller volume (i.e., the target cells are concentrated).

Figure 7:
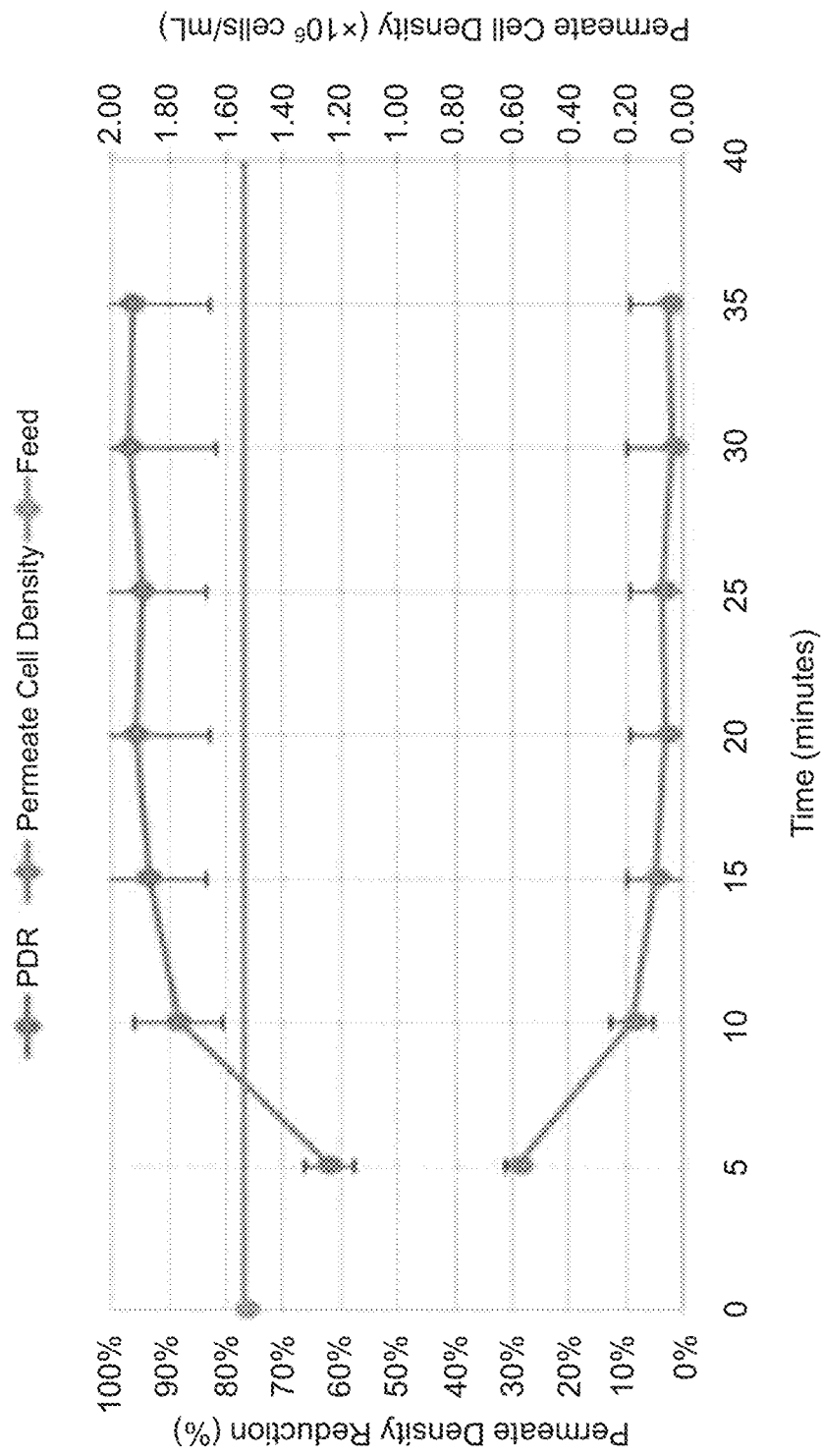
FIG. 7 is a graph showing the performance of the acoustophoretic device of FIG. 5. The x-axis is elapsed time (minutes) and runs from 0 to 40 in increments of 5. The left-side y-axis is permeate density reduction (%) and runs from 0 to 100 in increments of 10. The right-side y-axis is permeate cell density ($\times 10^6$ cells/mL) and runs from 0.00 to 2.00 in increments of 0.20. The uppermost solid line represents permeate reduction density (%). The lowermost solid line represents permeate cell density. The middle line running substantially horizontally across the page represents feed cell density for reference purposes.

FIG. 7 is a graph showing the performance of the acoustophoretic device of FIG. 5. The device was operated at a fixed frequency of 2.234 MHz for a mixture having a feed cell density of about 1.5×10⁶ cells/mL. As can be seen, the device achieved a permeate density reduction (PDR) of greater than 95% over about 35 minutes and a permeate cell density of less than 0.10×10⁶ cells/mL over the same time period.

Figure 8:
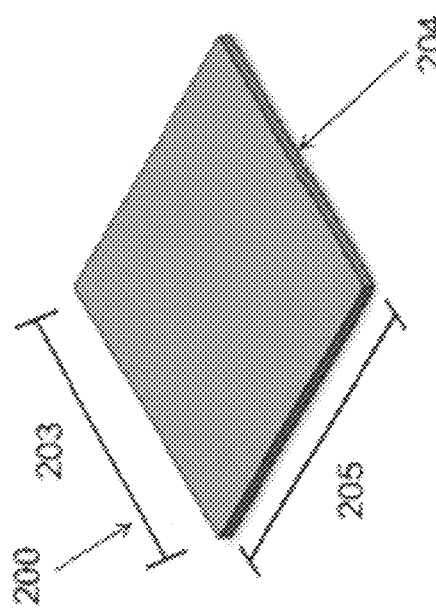
FIG. 8 is a conventional single-piece monolithic piezoelectric material used in an ultrasonic transducer.

The piezoelectric transducer(s) of the acoustophoretic devices and systems of the present disclosure can be single monolithic piezoelectric materials or can be made from an array of piezoelectric materials. The piezoelectric material can be a ceramic material, a crystal or a polycrystal, such as PZT-8 (lead zirconate titanate). FIG. 8 shows a monolithic, one-piece, single electrode piezoelectric crystal 200. The piezoelectric crystal has a substantially square shape, with a length 203 and a width 205 that are substantially equal to each other (e.g. about one inch). The crystal 200 has an inner surface 202, and the crystal also has an outer surface 204 on an opposite side of the crystal which is usually exposed to fluid flowing through the acoustophoretic device. The outer surface and the inner surface are relatively large in area, and the crystal is relatively thin (e.g. about 0.040 inches for a 2 MHz crystal).

Figure 9:
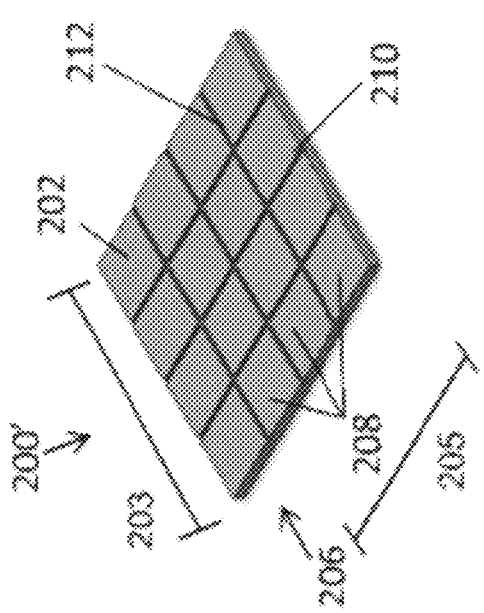
FIG. 9 is an example rectangular piezoelectric array having 16 piezoelectric elements used in the transducers of the present disclosure.

FIG. 9 shows a piezoelectric crystal 200' made from an array of piezoelectric materials. The inner surface 202 of this piezoelectric crystal 200' is divided into a piezoelectric array 206 with a plurality of (i.e. at least two) piezoelectric elements 208. However, the array is still a single crystal. The piezoelectric elements 208 are separated from each other by one or more channels or kerfs 210 in the inner surface 202. The width of the channel (i.e. between piezoelectric elements) may be on the order of from about 0.001 inches to about 0.02 inches. The depth of the channel can be from about 0.001 inches to about 0.02 inches. In some instances, a potting material 212 (e.g., epoxy, Sil-Gel, and the like) can be inserted into the channels 210 between the piezoelectric elements. The potting material 212 is non-conducting, acts as an insulator between adjacent piezoelectric elements 208, and also acts to hold the separate piezoelectric elements 208 together. Here, the array 206 contains sixteen piezoelectric elements 208 (although any number of piezoelectric elements is possible), arranged in a rectangular 4×4 configuration (square is a subset of rectangular). Each of the piezoelectric elements 208 has substantially the same dimensions as each other. The overall array 200' has the same length 203 and width 205 as the single crystal illustrated in FIG. 8.

Figure 10:
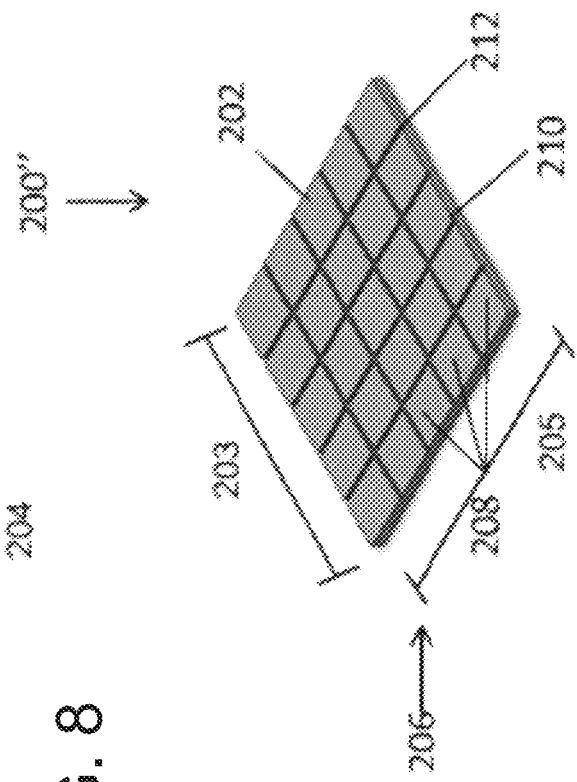
FIG. 10 is another example rectangular piezoelectric array having 25 piezoelectric elements used in the transducers of the present disclosure.

FIG. 10 shows another embodiment of a transducer 200". The transducer 200" is substantially similar to the transducer 200' of FIG. 9, except that the array 206 is formed from twenty-five piezoelectric elements 208 in a 5×5 configuration. Again, the overall array 200" has the same length 203 and width 205 as the single crystal illustrated in FIG. 8.

Figure 11:
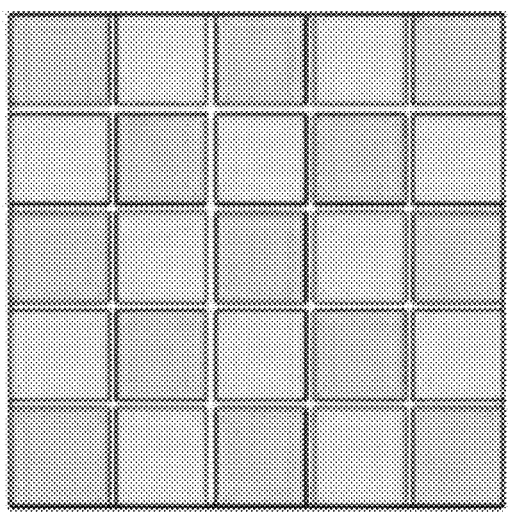
FIG. 11 is a diagram illustrating a piezoelectric material having 16 piezoelectric elements operated in out-of-phase modes. Dark elements indicate a 0° phase angle and light elements indicate a 180° phase angle.
Figure 11:
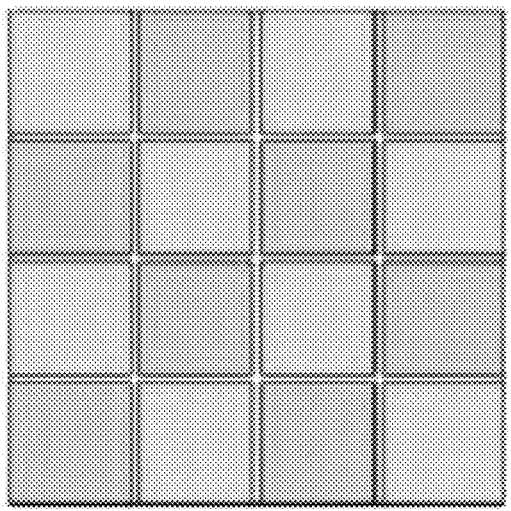

Each piezoelectric element in the piezoelectric array of the present disclosure may have individual electrical attachments (e.g. electrodes), so that each piezoelectric element can be individually controlled for frequency and power. These elements can share a common ground electrode. This configuration allows for not only the generation of a multi-dimensional acoustic standing wave, but also improved control of the acoustic standing wave. In this way, it is possible to drive individual piezoelectric elements (or multiple, separate ultrasonic transducers) with arbitrary phasing and/or different or variable frequencies and/or in various out-of-phase modes. For example, FIG. 11 illustrates an exemplary 0-180-0-180 mode, though additional modes can be employed as desired, such as a 0-180-180-0 mode. For example, for a 5×5 array, additional modes can be employed as desired, such as a 0-180-0-180-0 mode, a 0-0-180-0-0 mode, a 0-180-180-180-0 mode, or a 0-90-180-90-0 mode. The array could also be driven, for example, such that a checkerboard pattern of phases is employed, such as is shown in FIG. 11. In summary, a single ultrasonic transducer that has been divided into an ordered array can be operated such that some components of the array are out of phase with other components of the array.

The piezoelectric array can be formed from a monolithic piezoelectric crystal by making cuts across one surface so as to divide the surface of the piezoelectric crystal into separate elements. The cutting of the surface may be performed through the use of a saw, an end mill, or other means to remove material from the surface and leave discrete elements of the piezoelectric crystal between the channels/grooves that are thus formed.

Figure 12:
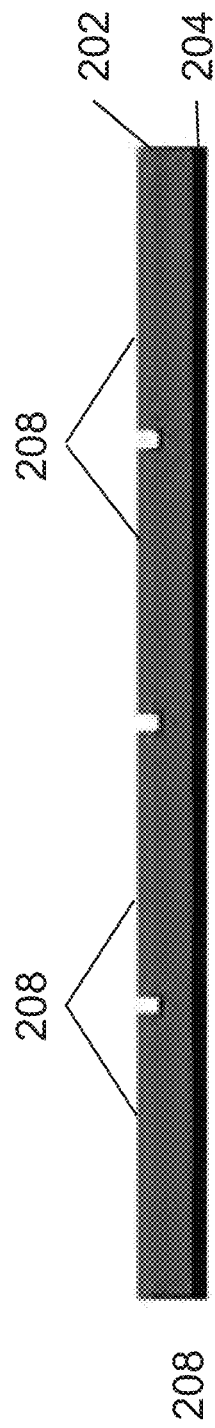
FIG. 12 illustrates a kerfed piezoelectric material (top) versus a transducer array that has piezoelectric elements joined together by a potting material (bottom).

As explained above, a potting material may be incorporated into the channels/grooves between the elements to form a composite material. For example, the potting material can be a polymer, such as epoxy. In particular embodiments, the piezoelectric elements 208 are individually physically isolated from each other. This structure can be obtained by filling the channels 210 with the potting material, then cutting, sanding or grinding the outer surface 204 down to the channels. As a result, the piezoelectric elements are joined to each other through the potting material, and each element is an individual component of the array. Put another way, each piezoelectric element is physically separated from surrounding piezoelectric elements by the potting material. FIG. 12 is a cross-sectional view comparing these two embodiments. On top, a crystal as illustrated in FIG. 9 is shown. The crystal is kerfed into four separate piezoelectric elements 208 on the inner surface 202, but the four elements share a common outer surface 204. On the bottom, the four piezoelectric elements 208 are physically isolated from each other by potting material 212. No common surface is shared between the four elements.

Figure 13:
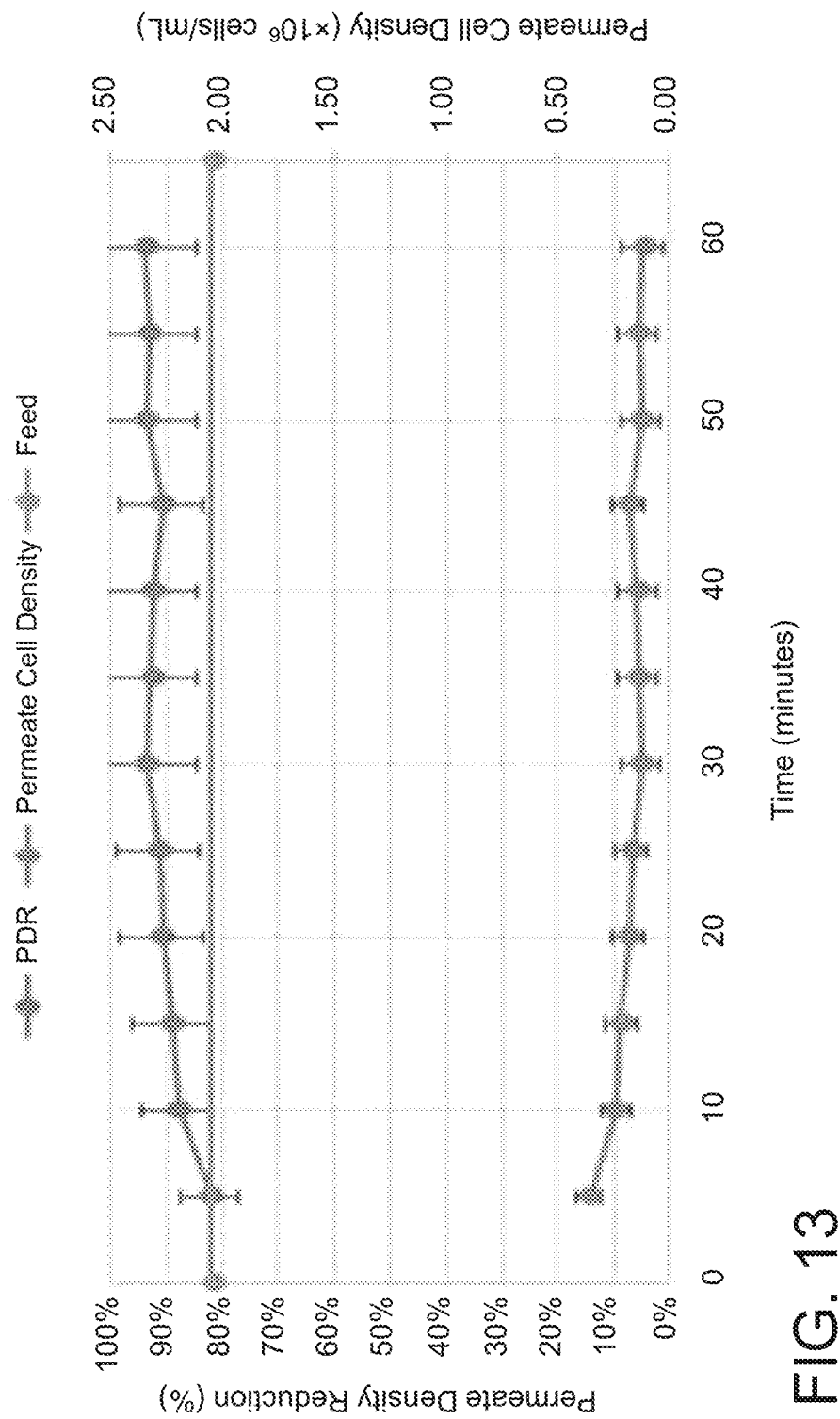
FIG. 13 is a graph showing the performance of an acoustophoretic device according to the present disclosure having a 16-element piezoelectric array, with the elements operated in-phase with one another. The x-axis is elapsed time (minutes) and runs from 0 to 60 in increments of 10. The left-side y-axis is permeate density reduction (%) and runs from 0 to 100 in increments of 10. The right-side y-axis is permeate cell density ($\times 10^6$ cells/mL) and runs from 0.00 to 2.50 in increments of 0.50. The uppermost solid line represents permeate reduction density (%). The lowermost solid line represents permeate cell density. The middle line running substantially horizontally across the page represents feed cell density for reference purposes.

FIG. 13 is a graph showing the performance of an acoustophoretic device according to the present disclosure having a 16-element piezoelectric array. The piezoelectric array was operated at a fixed frequency of 2.244 MHz for a mixture having a feed cell density of about 2.00×10⁶ cells/mL. As can be seen, the device achieved a permeate density reduction (PDR) of about 95% over about 60 minutes and a permeate cell density of about 0.10×10⁶ cells/mL over the same time period.

Figure 14:
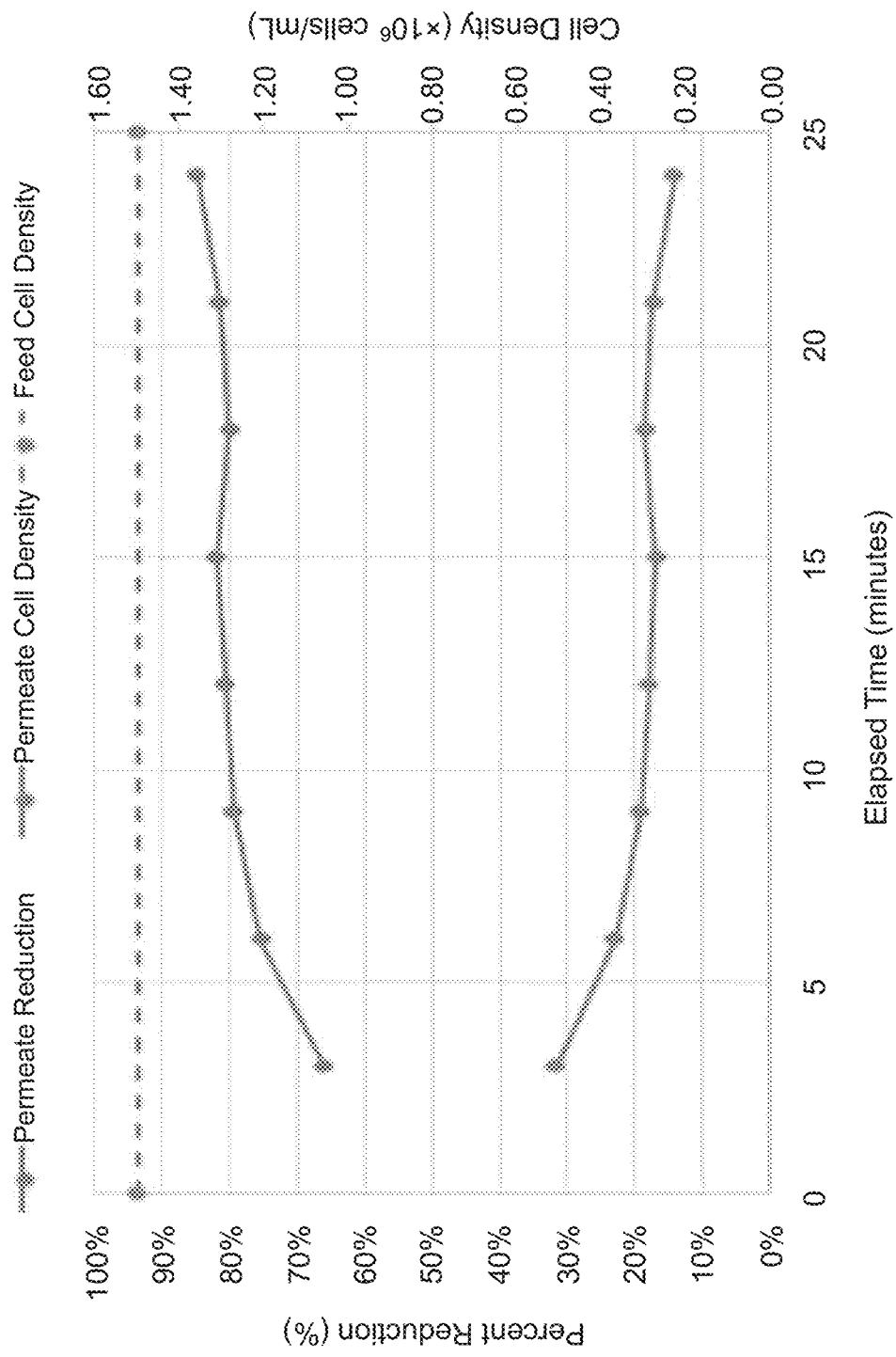
FIG. 14 is a graph showing the T-cell concentration performance of an acoustophoretic process according to the present disclosure with a low cell density culture. The x-axis is elapsed time (minutes) and runs from 0 to 25 in increments of 5. The left-side y-axis is percent reduction (%) and runs from 0 to 100 in increments of 10. The right-side y-axis is cell density ($\times 10^6$ cells/mL) and runs from 0.00 to 1.60 in increments of 0.20. The upper solid line represents permeate reduction (%). The lower solid line represents permeate cell density. The dashed line represents feed cell density for reference purposes.

The concentration efficiency of the acoustophoretic device was tested. First, a T-cell suspension having a cell density of 1×10⁶ cells/mL was used. A feed volume of between about 500 and 1000 mL was used at a flow rate of 10-15 mL/minute. The results are graphically depicted in FIG. 14. The device exhibited a concentration factor of between 10× and 20×, a 90% cell recovery, and a 77% washout efficiency (i.e., the amount of the first media that was displaced by the second media) over ten minutes of testing. A 10° C. temperature increase was observed.

Figure 15:
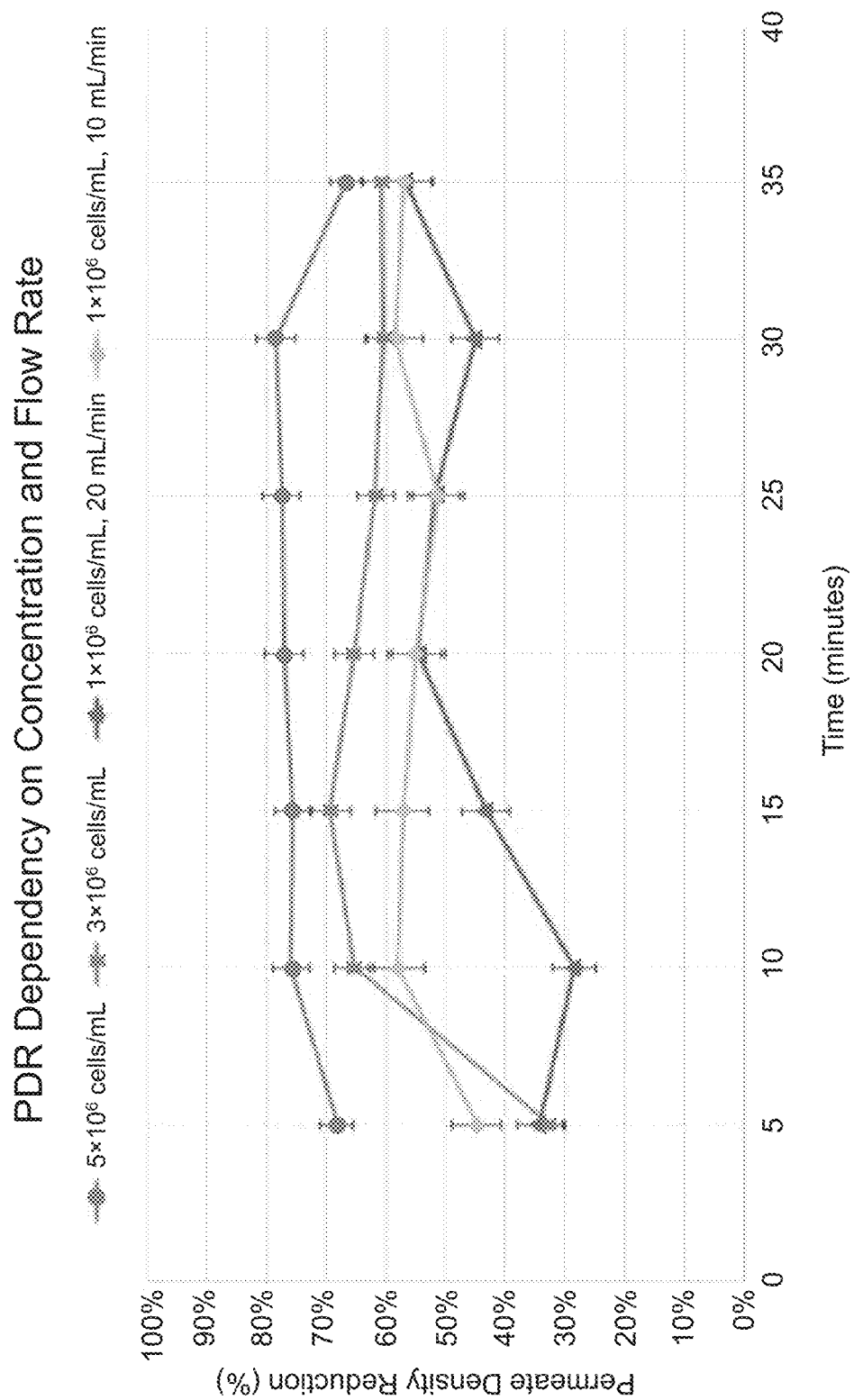
FIG. 15 is a graph showing the percent density reduction (PDR) dependency on concentration and flow rate for an acoustophoretic process according to the present disclosure. The x-axis is time (minutes) and runs from 0 to 40 in increments of 5. The y-axis is permeate density reduction (%) and runs from 0 to 100 in increments of 10. The line having circle-shaped data points represents a mixture having an initial cell concentration of $5 \times 10^6$ cells/mL. The line having x-shaped data points represents a mixture having an initial cell concentration of $3 \times 10^6$ cells/mL. The line having triangle-shaped data points represents a mixture having an initial cell concentration of $1 \times 10^6$ cells/mL at a flow rate of 20 mL/minute. The line having diamond-shaped data points represents a mixture having an initial cell concentration of $1 \times 10^6$ cells/mL at a flow rate of 10 mL/minute.

A yeast mixture was then used to test the dependency of the percent density reduction (PDR) on concentration and flow rate. The results are graphically depicted in FIG. 15. As seen here, the higher initial cell concentrations generally resulted in a greater PDR. Additionally, the varied flow rate (from 20 mL/min to 10 mL/min) did not have an observed effect on the PDR.

Figure 16:
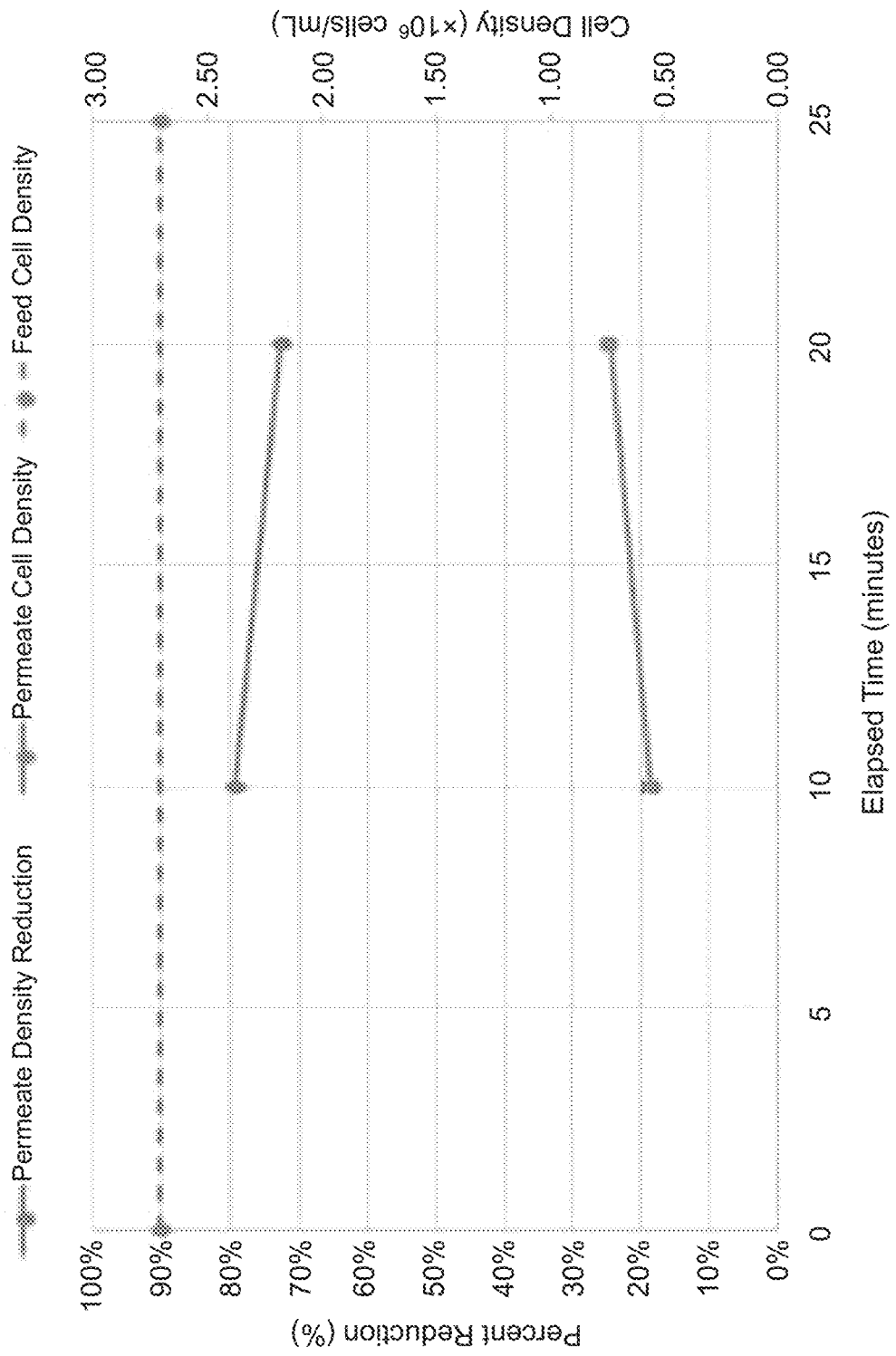
FIG. 16 is a graph showing the T-cell performance for an acoustophoretic process according to the present disclosure with a high cell density culture. The x-axis is elapsed time (minutes) and runs from 0 to 25 in increments of 5. The left-side y-axis is percent reduction (%) and runs from 0 to 100 in increments of 10. The right-side y-axis is cell density ($\times 10^6$ cells/mL) and runs from 0.00 to 3.00 in increments of 0.50. The upper solid line represents permeate density reduction (%). The lower solid line represents permeate cell density. The dashed line represents feed cell density for reference purposes.

The concentration efficiency of the acoustophoretic device was again tested with a higher cell density. A T-cell suspension having a cell density of 5×106 cells/mL was used. A feed volume of 1000 mL was used at a flow rate of 10-15 mL/minute. The results are graphically depicted in FIG. 16. The device exhibited a concentration factor of better than 10×, a 90% cell recovery, and a 77% washout efficiency over one hour of testing. A 10° C. temperature increase was again observed.

Figure 17B:
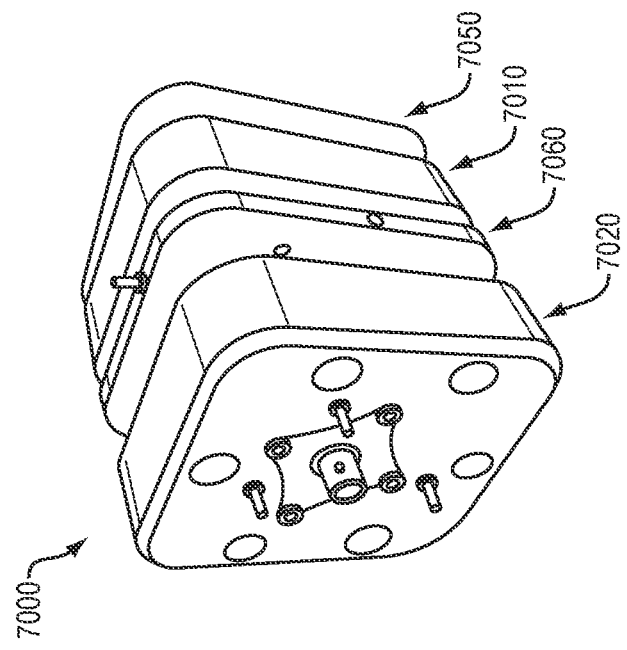
FIG. 17B is an exploded view of the device of FIG. 17A.
Figure 17A:
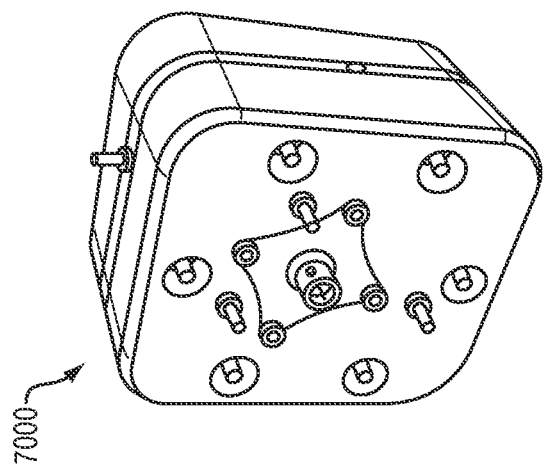
FIG. 17A is a perspective view of an example acoustophoretic device according to the present disclosure including a cooling unit for cooling the transducer.

During testing, it was also discovered that active cooling of the ultrasonic transducer led to greater throughput and efficiency and more power. As such, a cooling unit was developed for actively cooling the transducer. FIG. 17A illustrates an acoustophoretic device 7000 containing a cooling unit, in a fully assembled condition. FIG. 17B illustrates the device 7000, with the various components in a partially exploded view. Referring now to FIG. 17B, the device includes an ultrasonic transducer 7020 and a reflector 7050 on opposite walls of a flow chamber 7010. It is noted that the reflector 7050 may be made of a transparent material, such that the interior of the flow chamber 7010 can be seen. The ultrasonic transducer is proximate a first wall of the flow chamber. The reflector is proximate a second wall of the flow chamber or can make up the second wall of the flow chamber. A cooling unit 7060 is located between the ultrasonic transducer 7020 and the flow chamber 7010. The cooling unit 7060 is thermally coupled to the ultrasonic transducer 7020. In this figure, the cooling unit is in the form of a thermoelectric generator, which converts heat flux (i.e. temperature differences) into electrical energy using the Seebeck effect, thus removing heat from the flow chamber. Put another way, electricity can be generated from undesired waste heat while operating the acoustophoretic device.

It is noted that the various inlets and outlets (e.g. fluid inlet, concentrate outlet, permeate outlet, recirculation outlet, bleed/harvest outlet) of the flow chamber are not shown here. The cooling unit can be used to cool the ultrasonic transducer, which can be particularly advantageous when the device is to be run continuously with repeated processing and recirculation for an extended period of time (e.g., perfusion).

Alternatively, the cooling unit can also be used to cool the fluid running through the flow chamber 7010. For desired applications, the cell culture should be maintained around room temperature (~20° C.), and at most around 28° C. This is because when cells experience higher temperatures, their metabolic rates increase. Without a cooling unit, however, the temperature of the cell culture can rise as high as 34° C.

These components are modular and can be changed or switched out separately from each other. Thus, when new revisions or modifications are made to a given component, the component can be replaced while the remainder of the system stays the same.

The goal is to begin with a culture bag having a volume of about 1 liter (L) to about 2 L, with a density of about 1 million cells/m L, and concentrate this bag to a volume of about 25 mL to about 30 mL, and then to wash the growth media or exchange the media within a time of about one hour (or less). Desirably, the system can be made of materials that are stable when irradiated with gamma radiation.

Figure 18:
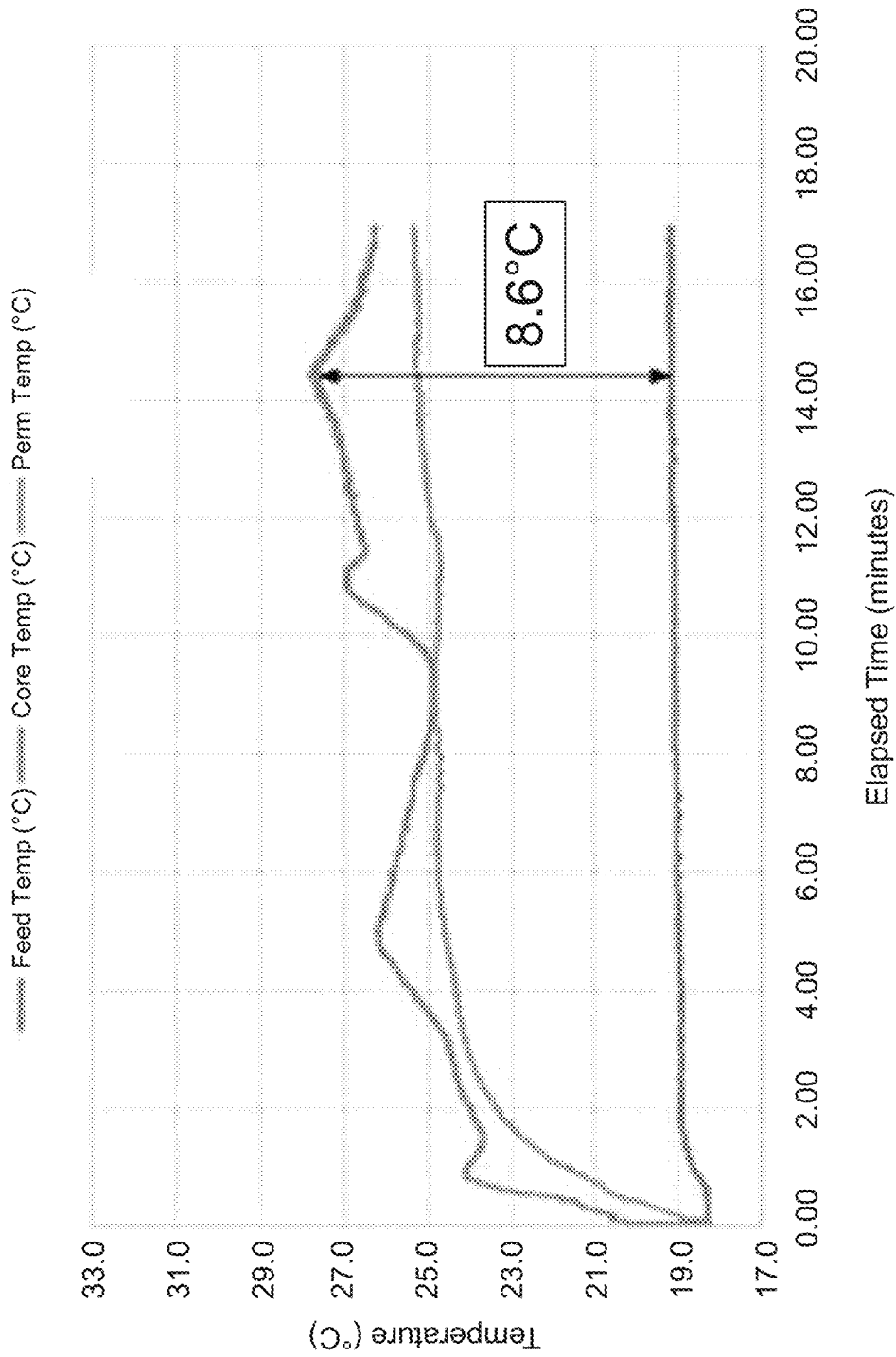
FIG. 18 is a graph showing the temperature profile of an acoustophoretic device without active cooling. The x-axis is elapsed time (minutes) and runs from 0.00 to 20.00 in increments of 2.00. The y-axis is temperature (° C.) and runs from 17.00 to 33.00 in increments of 2.00. The lowermost line along the right side of the graph represents the feed temperature (° C.). The uppermost line along the right side of the graph represents the core temperature (° C.). The middle line along the right side of the graph represents the permeate temperature (° C.).
Figure 19:
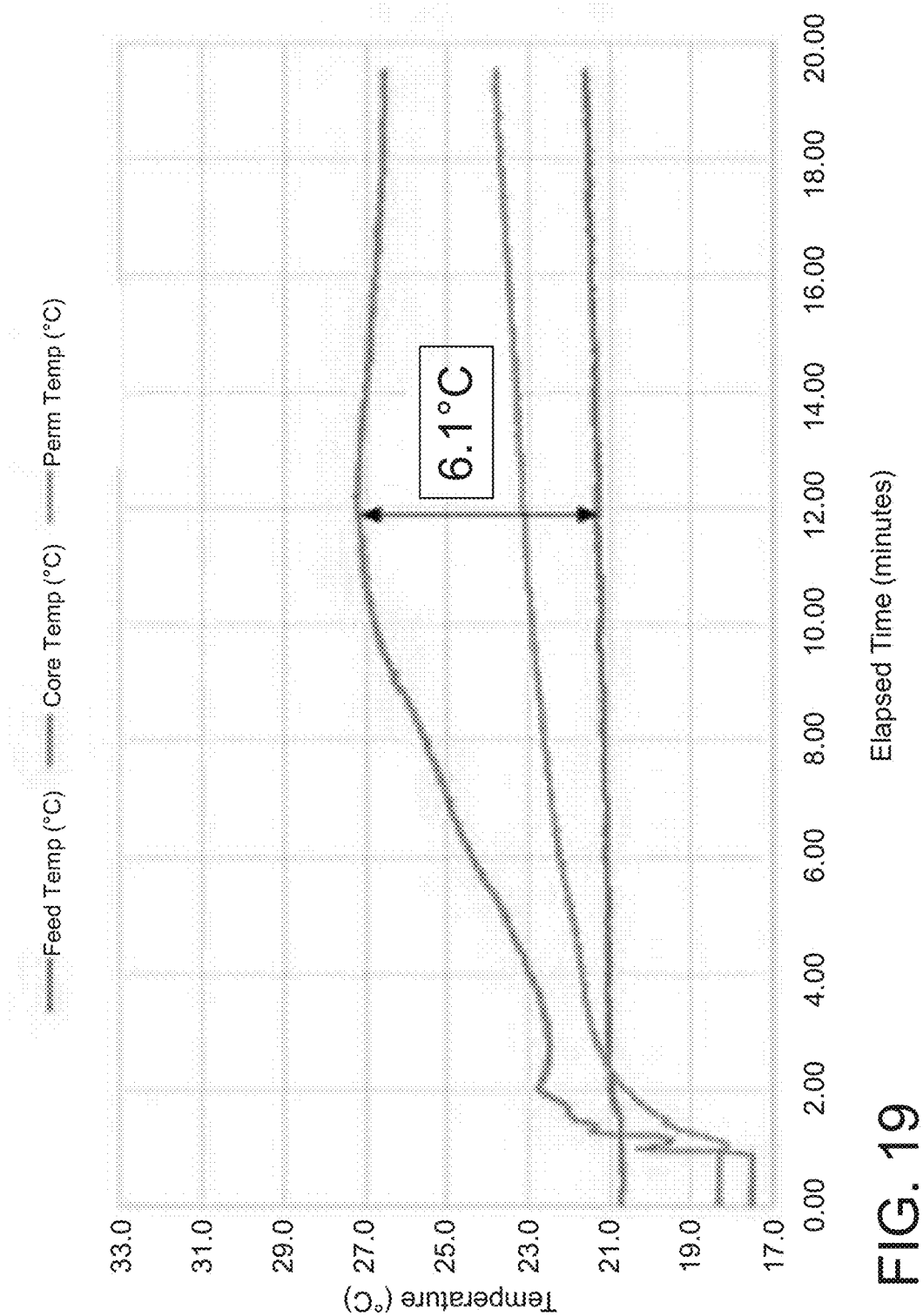
FIG. 19 is a graph showing the temperature profile of an acoustophoretic device with active cooling of the transducer. The x-axis is elapsed time (minutes) and runs from 0.00 to 20.00 in increments of 2.00. The y-axis is temperature (° C.) and runs from 17.00 to 33.00 in increments of 2.00. The lowermost line along the right side of the graph represents the feed temperature (° C.). The uppermost line along the right side of the graph represents the core temperature (° C.). The middle line along the right side of the graph represents the permeate temperature (° C.).

The advantages of providing a cooling unit for the transducer can be seen in FIG. 18 and FIG. 19. FIG. 18 graphically shows the temperature profile of the acoustophoretic device without any active cooling (e.g., without a cooling unit for the transducer). As seen in FIG. 18, the temperature difference between the feed and the core (e.g., the transducer) was 8.6° C. FIG. 19 graphically shows the temperature profile of the acoustophoretic device with active cooling (e.g., with a cooling unit for the transducer). As seen in FIG. 19, through the use of active cooling the temperature difference between the feed and the core was reduced to 6.1° C.

Figure 20:
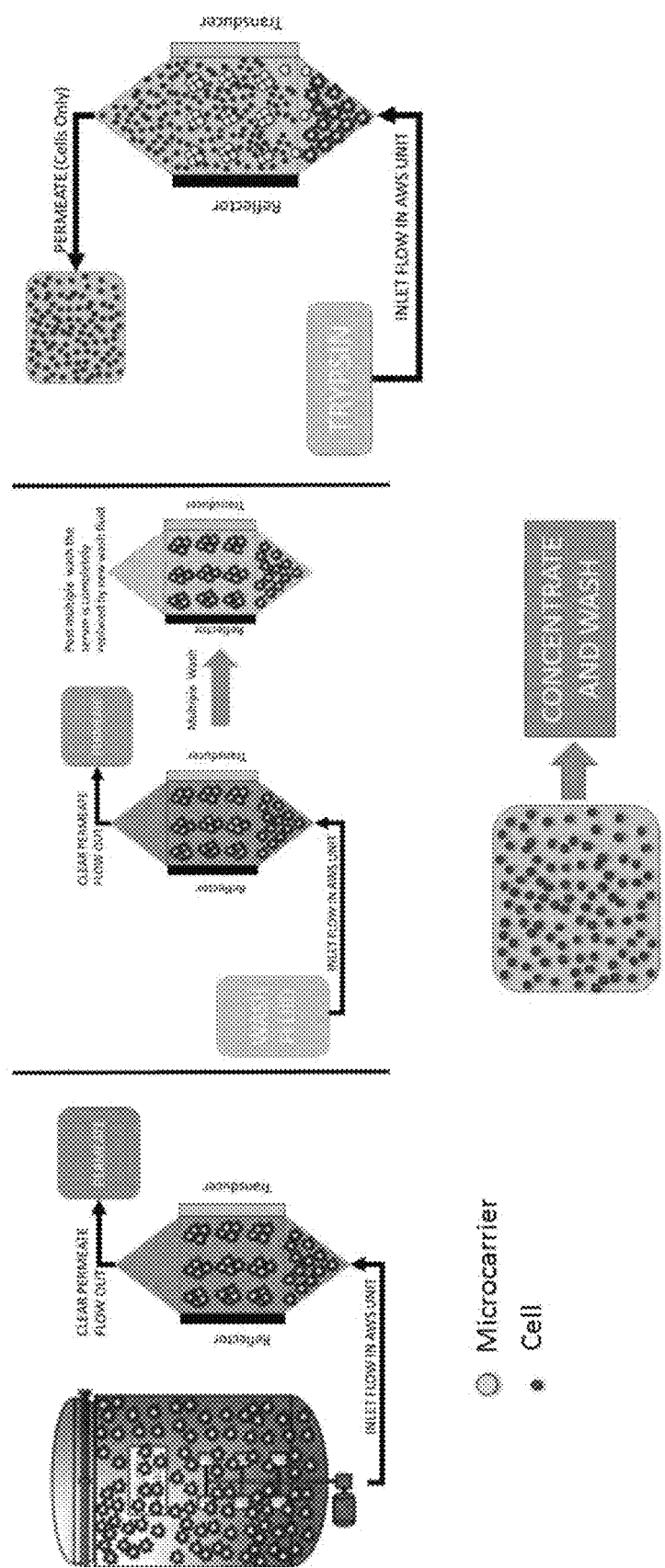
FIG. 20 illustrates a process for concentrating, washing, and/or separating microcarriers and cells according to the present disclosure. The leftmost portion represents a first step of receiving complexes of microcarriers and cells surrounded by a bioreactor serum from a bioreactor and concentrating the microcarrier/cell complexes in an acoustophoretic device according to the present disclosure. The middle portion represents a second step of washing the concentrated microcarriers with attached cells to remove the bioreactor serum. The rightmost portion represents a third step of trypsinizing, or disassociating, the microcarriers and cells and a fourth step of separating the microcarriers from the cells. The bottom portion represents a final wash and concentrate step that can be employed as desired.

FIG. 20 illustrates a four-step process (with an optional fifth step) for concentrating, washing, and separating microcarriers from cells. The first step in the process involves concentrating the microcarriers with attached cells in an acoustophoretic device, such as those described herein. The microcarriers and attached cells can be introduced to the acoustophoretic device by receiving the microcarriers with attached cells from a bioreactor. In the bioreactor, the microcarriers and cells are suspended in a first media (e.g., growth serum or preservative material used to keep the cells viable in the bioreactor). The microcarriers with attached cells surrounded by the first media are concentrated by the acoustic standing wave(s) generated in the acoustophoretic device. In a second step, the concentrated microcarriers with attached cells are then washed with a second media to remove the first media (e.g., bioreactor growth serum or preservative material). The third step is to then introduce a third media containing an enzyme into the acoustophoretic device to detach the cells from the microcarriers through enzymatic action of the second media. In particular embodiments, trypsin is the enzyme used to enzymatically detach the cells from the microcarriers. The multi-dimensional acoustic standing wave can then be used to separate the cells from the microcarriers. Usually, this is done by trapping the microcarriers in the multi-dimensional acoustic standing wave, while the detached cells pass through with the third media. However, the cells can be trapped instead, if desired. Finally, the separated cells may optionally be concentrated and washed again, as desired.

After being concentrated and trapped/held in the multi-dimensional acoustic standing wave, the microcarriers can coalesce, clump, aggregate, agglomerate, and/or cluster to a critical size at which point the microcarriers fall out of the acoustic standing wave due to enhanced gravitational settling. The microcarriers can fall into a collector of the acoustophoretic device located below the acoustic standing wave, to be removed from the flow chamber.

Figure 21:
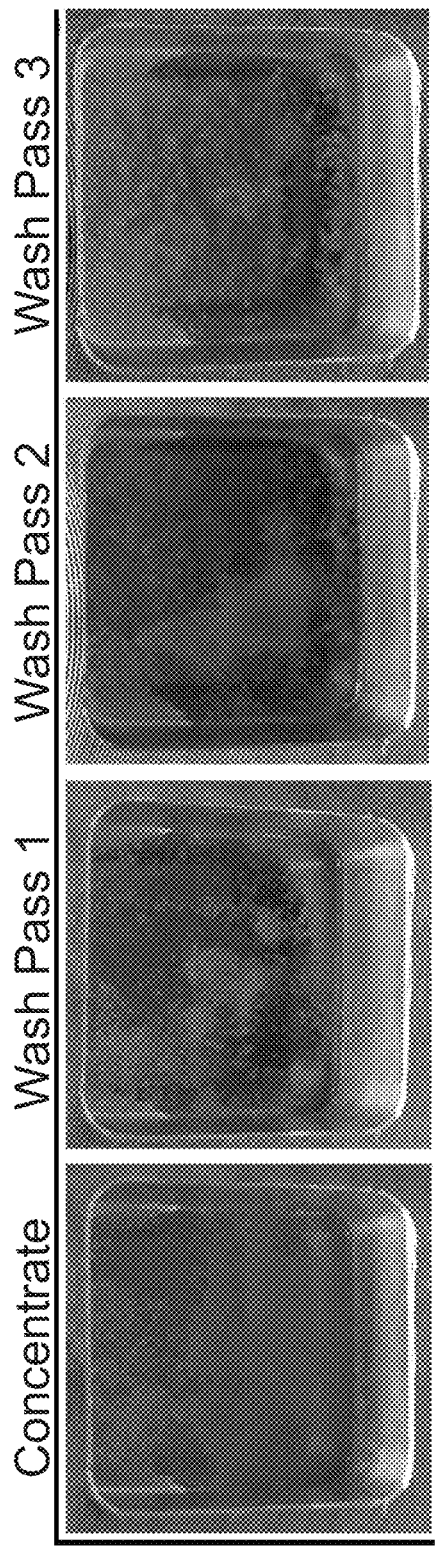
FIG. 21 shows media exchange in an acoustophoretic device according to the present disclosure. The "Concentrate" photograph shows the concentrate (e.g., concentrated microcarriers with attached T cells) surrounded by a first media (dyed red). The "Wash Pass 1" photograph shows the microcarriers with attached T cells after a first wash pass using a second media (dyed blue). The "Wash Pass 2" photograph shows the microcarriers with attached T cells after a second wash pass. The rightmost "Wash Pass 3" photograph shows the microcarriers with attached T cells after a third wash pass, and is almost completely blue.

During testing, steps one and two (i.e., concentration and washing) were performed using red and blue food dye to make colored fluid. The concentration mixture included SoloHill microcarriers in red fluid. The wash mixture included blue fluid and was passed through the device three times. The concentrate was observed under a microscope, as shown in the leftmost image of FIG. 21. The concentration step was shown to have a 99% efficiency. The remaining three images in FIG. 21 show microscopic images after the first, second, and third wash passes, respectively. As seen from left to right in FIG. 21, the first media (dyed red) is progressively washed out by a second media (dyed blue) over a series of wash passes. The light absorbance data is shown in the table below.

|  | Light Absorbance | |
| --- | --- | --- |
| Sample | Red (510 nm) | Blue (630 nm) |
| Feed | 0.138 | 0.041 |
| Wash Pass 1 | 0.080 | 0.066 |
| Wash Pass 2 | 0.063 | 0.080 |
| Wash Pass 3 | 0.054 | 0.084 |

The decrease in red light absorbance and increase in blue light absorbance evidences the feasibility of the washing steps.

Figure 22:
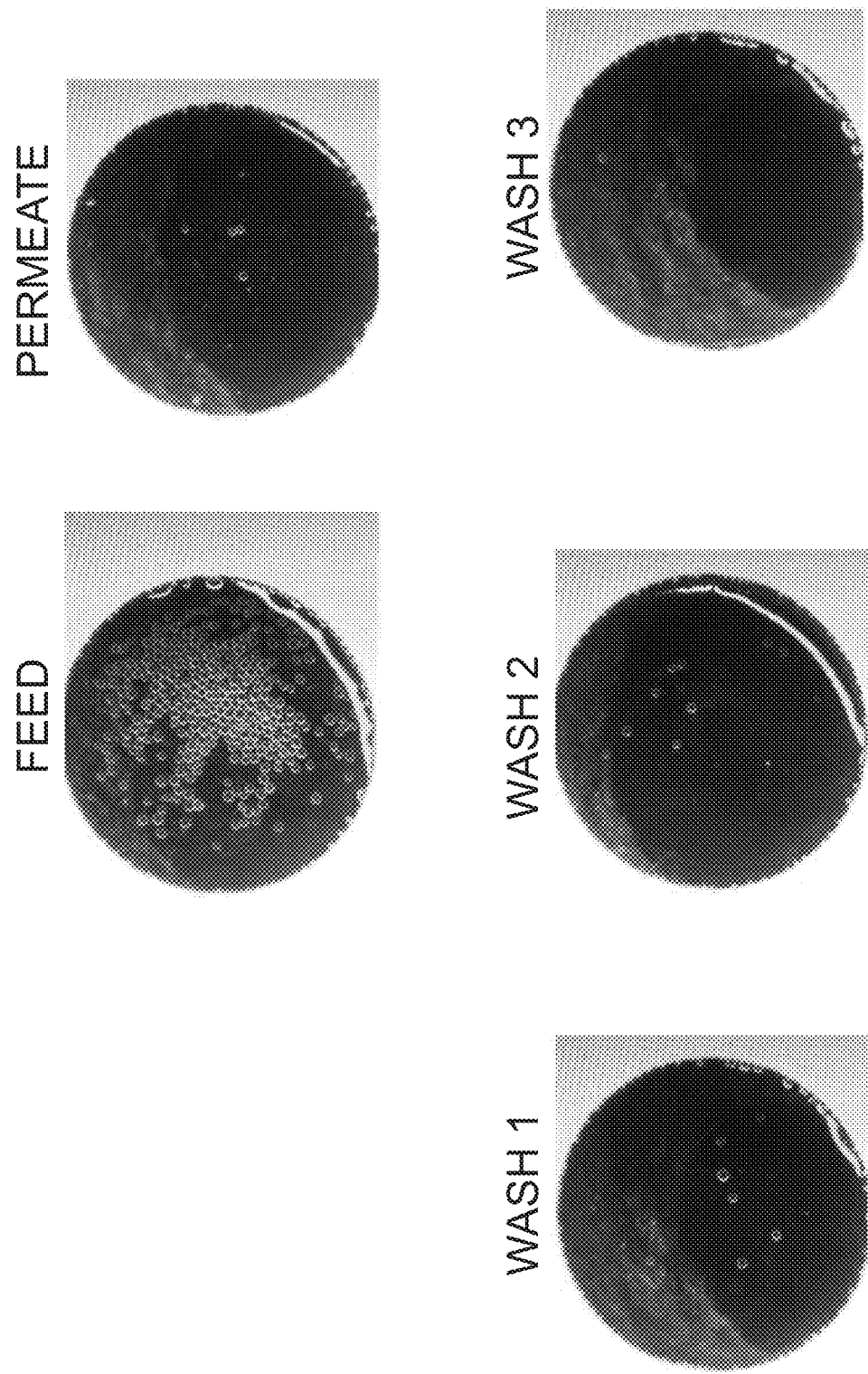
FIG. 22 shows microscopic images of the media exchange shown in FIG. 21.

FIG. 22 shows microscopic images of the microcarriers and attached cells during the concentration and washing steps. In particular, the leftmost image in the top row shows the microcarriers and attached cells in the feed, prior to introduction into the acoustophoretic device. The rightmost image in the top row shows the microcarriers and attached cells in the permeate, after concentration in the acoustophoretic device. The bottom row of images show the microcarriers and attached cells in the device during the washing step, namely during the first, second, and third wash passes, from left to right.

Figure 23:
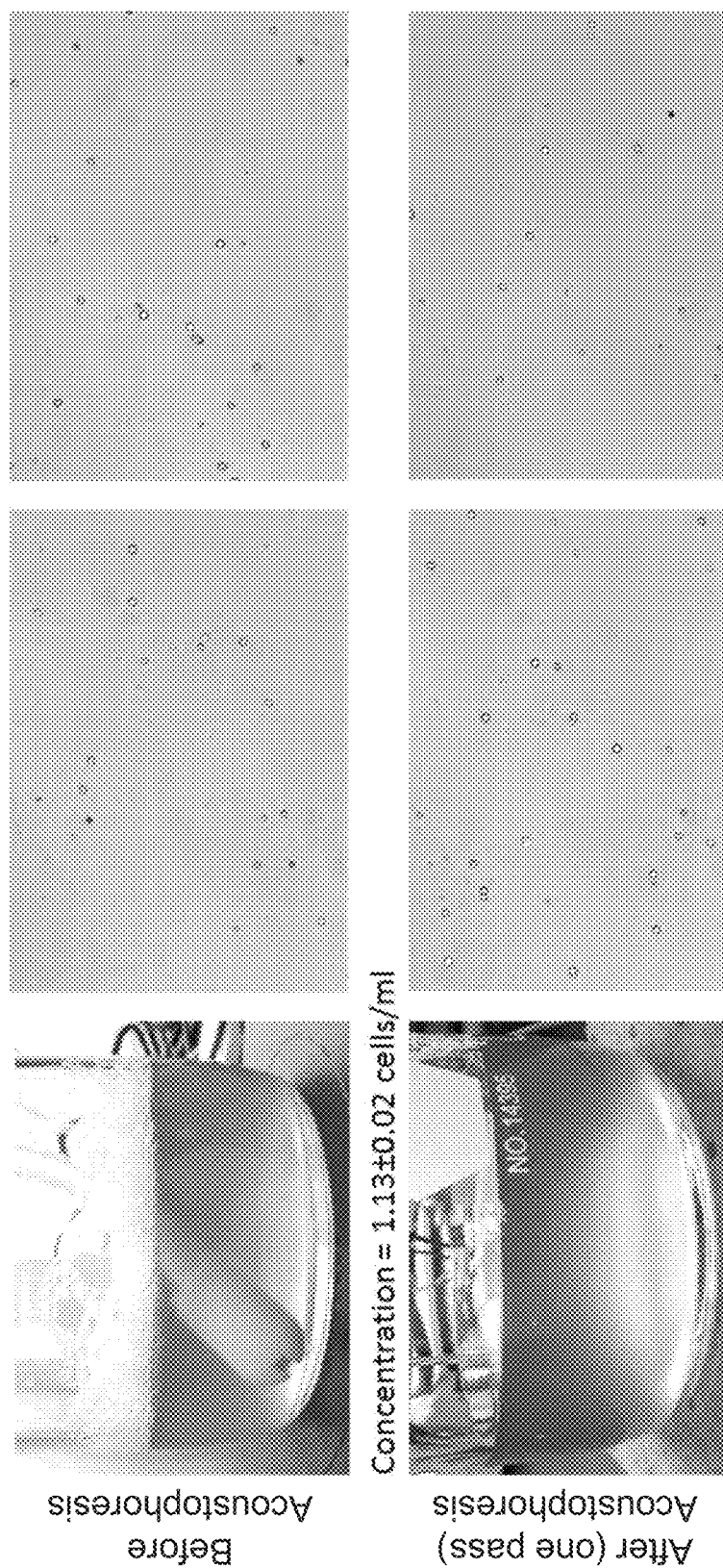
FIG. 23 shows the concentration of T cells in the acoustophoretic device before acoustophoresis (top row of photographs) and after one acoustophoresis pass (bottom row of photographs).

FIG. 23 shows the concentration of T-cells after being separated in the acoustophoretic device. The top row of images show the T-cells before acoustophoresis with a concentration of $1.14\pm0.03\times10^6$ cells/mL. The bottom row of images show the T-cells after acoustophoresis with a concentration of $1.13\pm0.02\times10^6$ cells/mL. The comparable concentrations evidence that substantially all of the cells pass through the acoustophoretic device, as the concentration was substantially unchanged by acoustophoresis.

Figure 24:
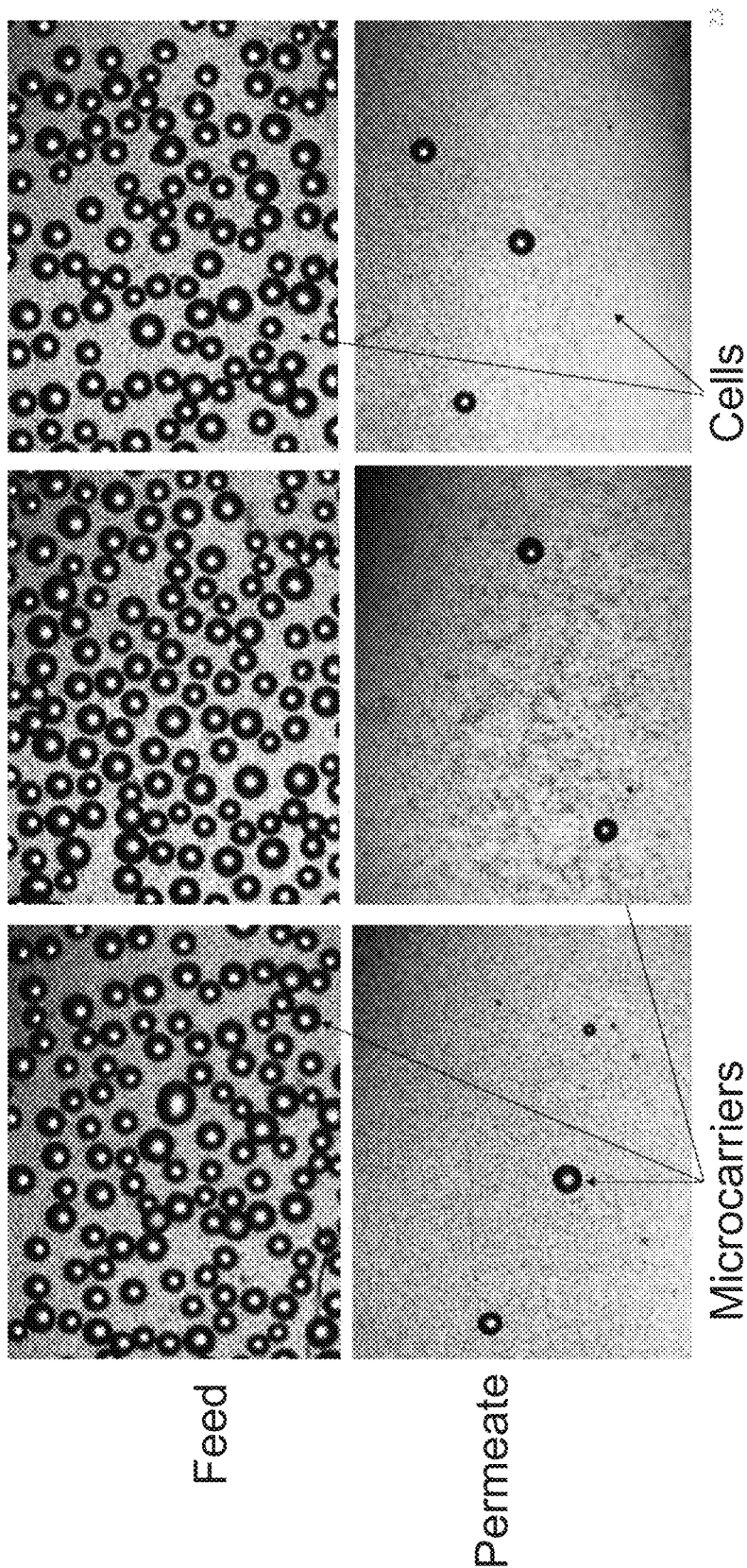
FIG. 24 shows the concentration of microcarriers with attached T cells in the feed into the acoustophoretic device (top row of photographs) and the concentration of separated microcarriers and T cells in the permeate drawn out of the acoustophoretic device (bottom row of photographs). The dark circular items indicate microcarriers, and the lighter area indicates T cells.
Figure 25:
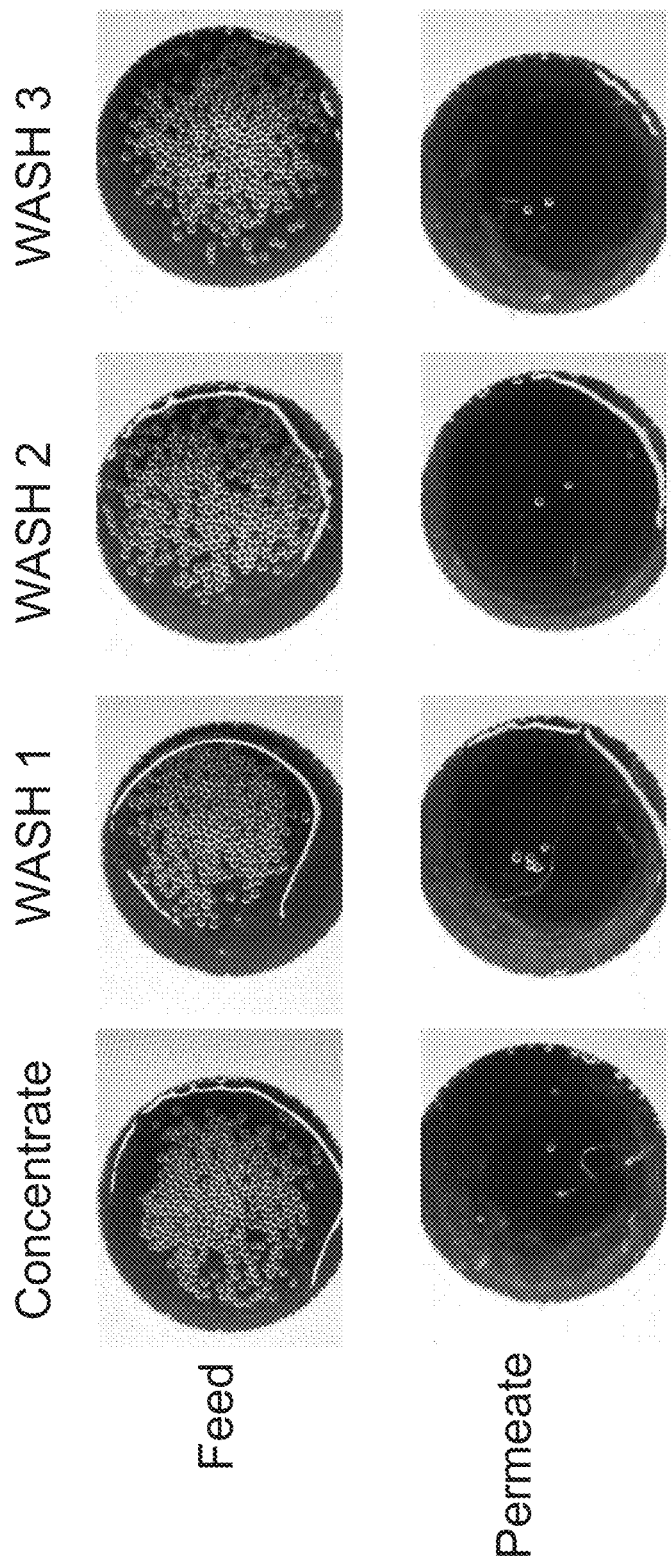
FIG. 25 shows microscopic images of the concentration of microcarriers with attached T cells in the feed and the concentration of separated microcarriers and T cells in the permeate.

FIG. 24 shows the presence of SoloHill microcarriers and T-Cells in the acoustophoretic device under 4× magnification. The top row of images show the microcarriers and cells in the feed before acoustophoresis. The bottom row of images show the microcarriers and cells in the permeate after the cells have been separated out by acoustophoresis. The difference in the number of microcarriers with the application of acoustophoresis evidences the feasibility of using the device for trapping the microcarriers in the device and separating the cells therefrom. The feasibility of this technique and the results are further evidenced by the images in FIG. 25, which show microscopic images of the microcarriers and cells in the feed (top row of images) and permeate (bottom row of images) after concentration and the first, second, and third washes, from left to right.

The testing of the acoustophoretic concentrating, washing, and separating process showed that the process is appropriate for cell therapy and microcarrier applications. The concentrate and wash steps were performed with a resulting efficiency of greater than 99%, and the separating step e.g., separating the cells from the microcarriers, was performed with greater than 98% efficiency.

Figure 26:
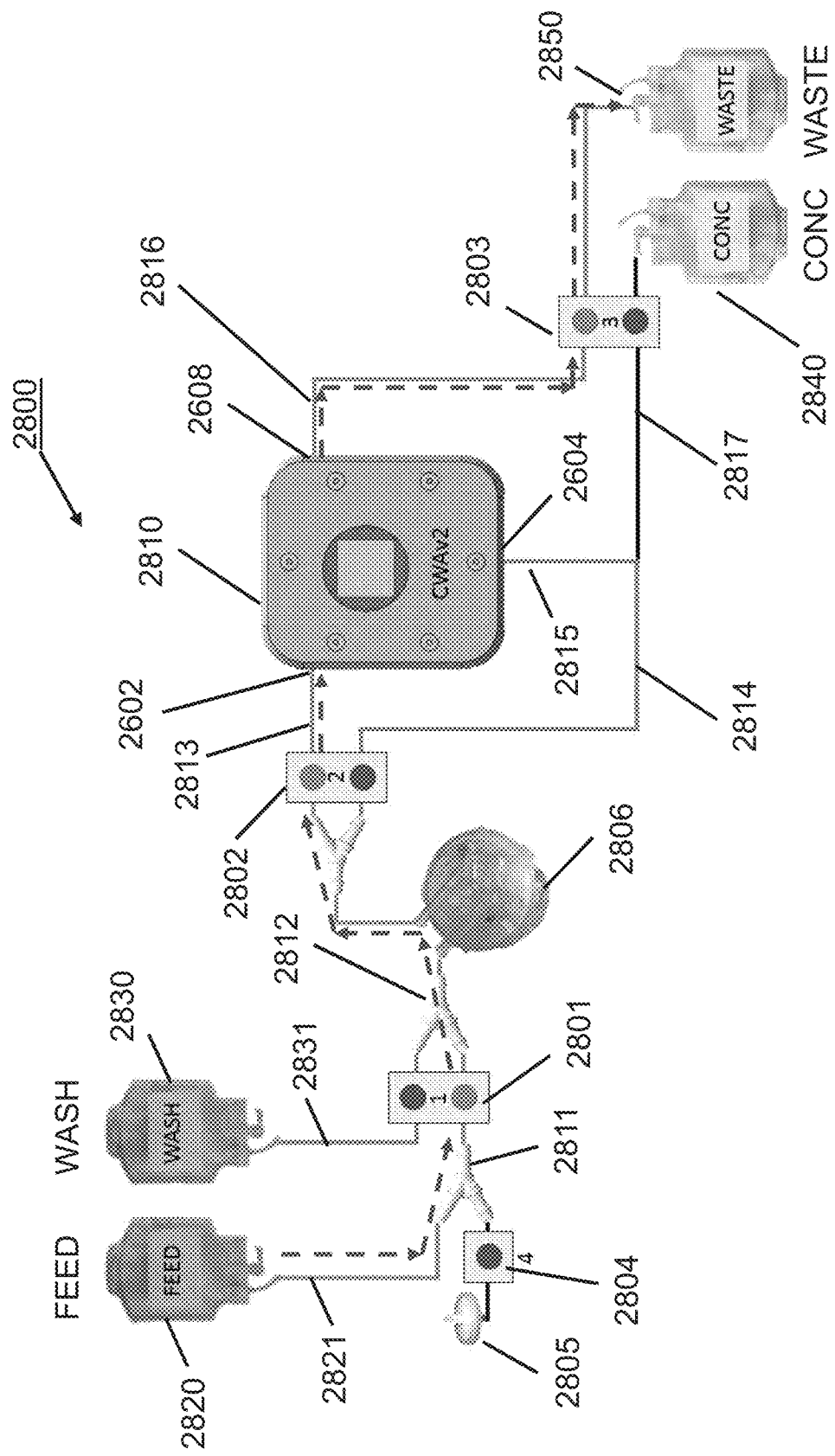
FIG. 26 is a schematic of an example acoustophoretic system according to the present disclosure showing the flow path of the feed material through the system.
Figure 27:
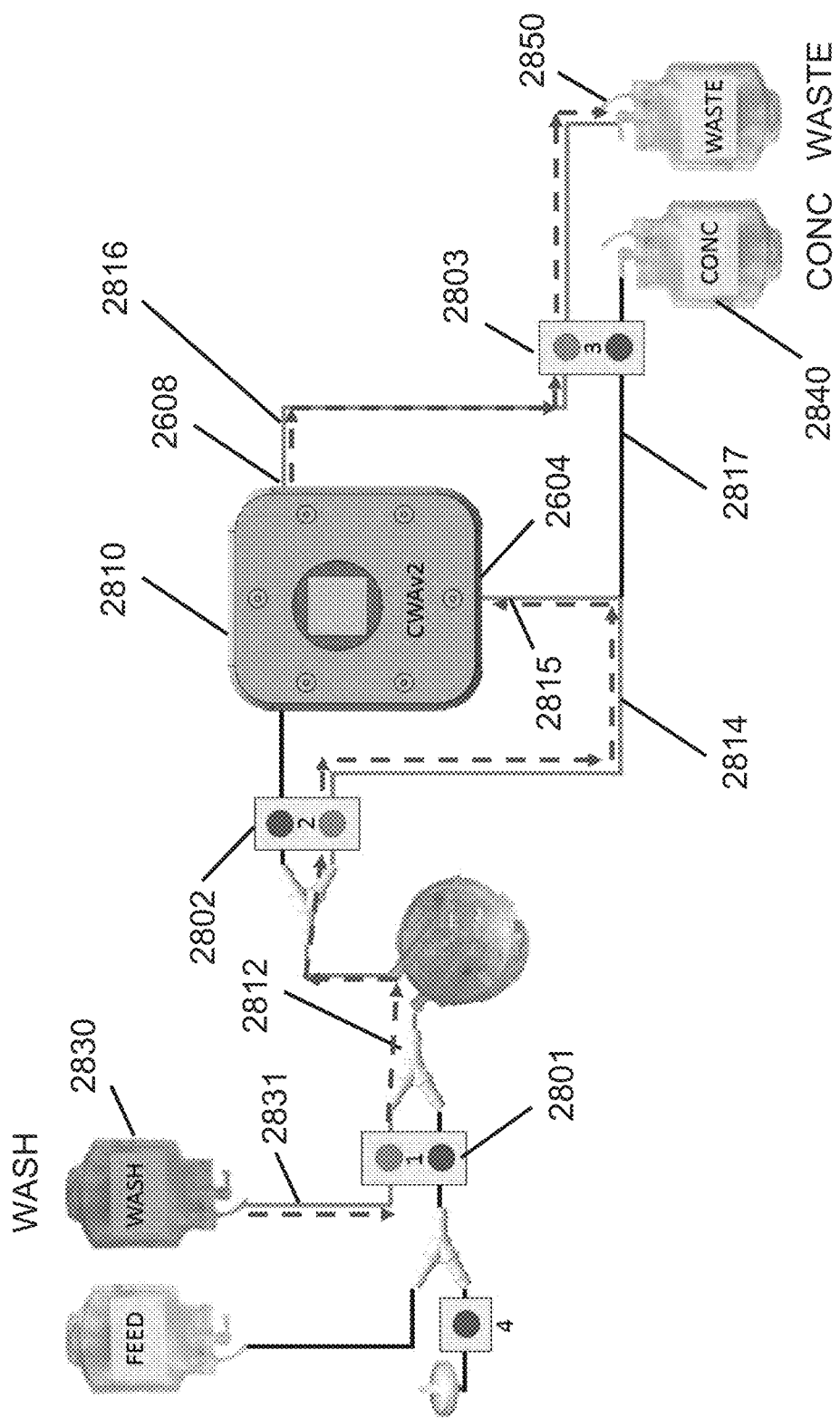
FIG. 27 is a schematic of the example acoustophoretic system of FIG. 28 showing the flow path of the wash material through the system.
Figure 28:
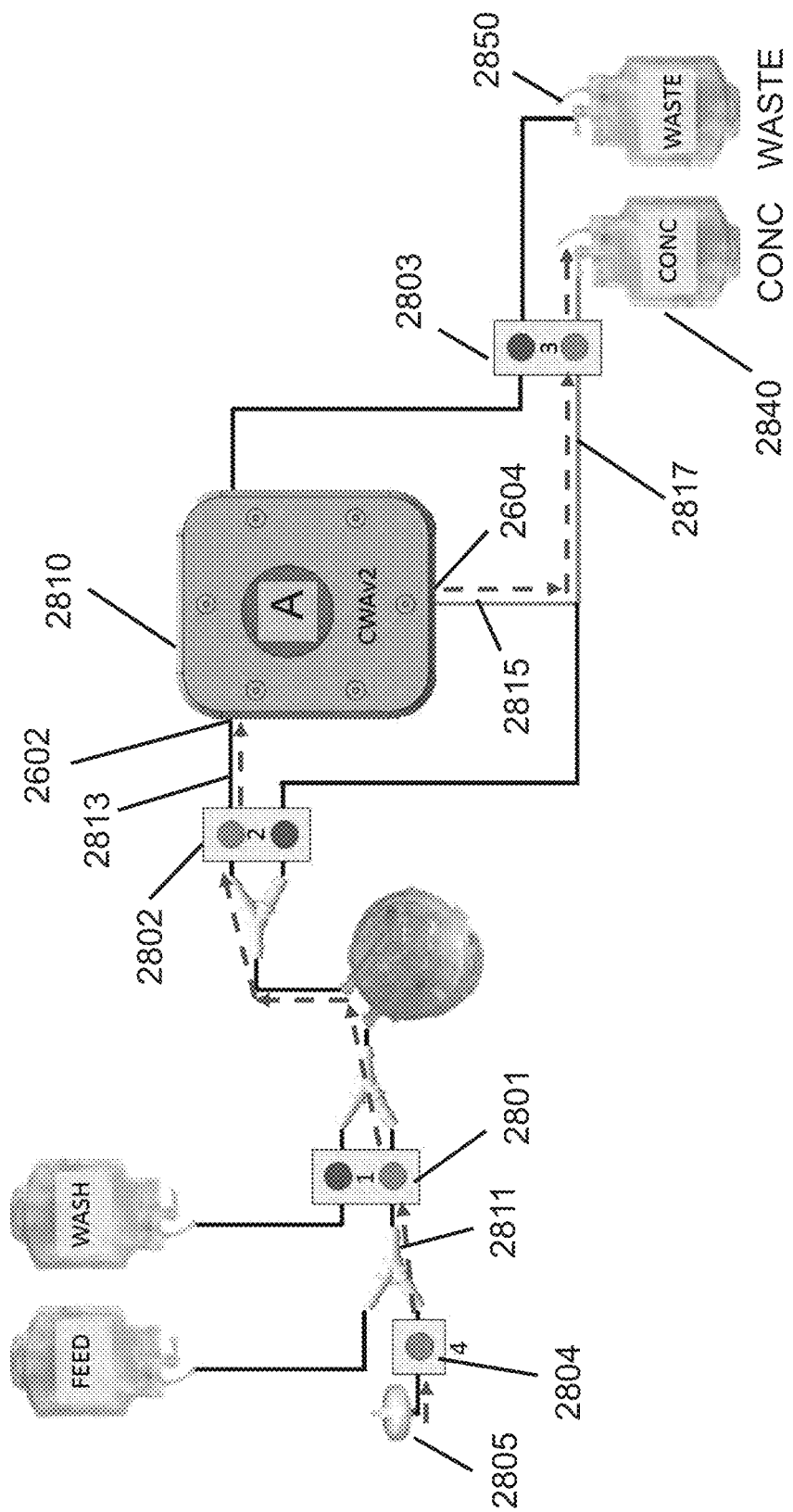
FIG. 28 is a schematic of the example acoustophoretic system of FIG. 28 showing draining of the system.

FIGS. 26-28 illustrate another example embodiment of an acoustophoretic system/process 2800 including a disposable acoustophoretic device 2810 with solenoid pinch valves that control the flow of fluid therethrough. Starting from the left-hand side of FIG. 26, the system includes a feed tank 2820, a wash tank 2830, and an air intake 2805. The air intake 2805 runs through an air intake valve 2804. Feed line 2821 runs from the feed tank 2820. The air intake and the feed line 2821 are joined together by a Y-connector into common feed line 2811, which runs into feed selector valve 2801. A wash line 2831 runs from the wash tank 2830, and also runs into feed selector valve 2801. Feed selector valve 2801 permits only one line to be open at a given time (valves 2802, 2803 also operate in this manner). Wash line 2831 and feed line 2811 are joined together by a Y-connector downstream of the feed selector valve 2801 into input line 2812. Input line 2812 passes through pump 2806 to inflow selector valve 2802, which is downstream of the feed selector valve 2801 and upstream of the acoustophoretic device 2810. The inflow selector valve 2802 selectively controls the inflow of feed or wash into the acoustophoretic device 2810 through either feed port 2602 or wash/drain port 2604. A feed line 2813 runs from the inflow selector valve 2802 to feed port 2602. A wash line 2814 runs from the inflow selector valve 2802 to common line 2815 and into wash/drain port 2604.

On the right-hand side of FIG. 26, an outflow selector valve 2803 is located downstream of the acoustophoretic device 2810 and controls the outflow of fluid therefrom. A waste line 2816 runs from waste port 2608 through outflow selector valve 2803 and subsequently to waste tank 2850. The common line 2815 runs into drain line 2817, which then passes through outflow selector valve 2803 and subsequently to concentrate tank 2840. These tanks 2840, 2850 can be, for example, collection bags. The outflow selector 2803 thereby selectively controls the flow of fluid to the concentrate tank and waste tank.

The use of collection bags at the ends of the concentrate and waste lines advantageously creates an enclosed primary environment within which concentration, washing, and/or separation of cells and cellular materials can occur, which helps to prevent the cells/cell culture/cellular material from being exposed to possible intrusions, pathogens, or outside cellular influences that would be harmful.

FIG. 26 also illustrates the flow path of the feed material through the system. In this example embodiment, feed selector valve 2801 is operated with the bottom open (and top closed), so that the feed from feed tank 2820 flows through. Inflow selector valve 2802 is operated with the top open (and bottom closed), so that the feed material enters the acoustophoretic device 2810 via feed port 2602. The outflow selector valve 2803 is also operated with the top open (and bottom closed) so that the fluid/first media of the feed material flows through to waste tank 2850. The targeted particles in the feed material (e.g., microcarriers or cells) are trapped in the acoustophoretic device 2810 by action of a multi-dimensional acoustic standing wave(s), as explained in detail herein.

FIG. 27 illustrates the flow path of the wash material through the system. Feed selector valve 2801 is operated with the top open (and bottom closed), so that the wash material from wash tank 2830 flows through. The inflow selector valve 2802 is operated with the bottom open (and top closed) and the outflow selector valve 2803 is operated with the top open (and bottom closed). As a result, the wash material enters the acoustophoretic device 2810 via wash/drain port 2604, which operates as a wash inlet. Note that the closed outflow selector valve 2803 prevents the wash material from entering concentrate tank 2840. The wash material can then pass through the acoustophoretic device 2810 and remove the first media (e.g., bioreactor serum or preservative material). The wash material then exits via waste port 2608 and flows to waste tank 2850. The target particles remain trapped in the acoustophoretic device 2810.

FIG. 28 illustrates the draining of the system (e.g., the collection of the target particles). Air intake valve 2804 is opened. The feed selector valve 2801 is operated with the bottom open (and top closed), and the inflow selector valve 2802 is operated with the top open (and bottom closed), so that air enters the acoustophoretic device 2810 via feed port 2602. The air generally aids in dislodging the clusters of target particles from the acoustophoretic device 2810. The outflow selector valve 2803 is operated with the bottom open (and top closed). The target particles flow out of wash/drain port 2604 through common line 2815, through drain line 2817 and subsequently to concentrate tank 2840.

Concentrating and washing cell culture is useful for producing biological products for industrial use. The systems of the present disclosure can be continuously improved and scaled up for handling of larger volumes.

In some examples, the acoustophoretic devices of the present disclosure may have a concentrated volume ranging from about 25 mL to about 75 mL. The devices may have a total cell capacity of about 4 billion to about 40 billion cells, or from about 4 billion to about 8 billion cells, or from about 20 billion to about 40 billion cells, or from about 16 billion to about 35 billion cells. The fluids entering and exiting the acoustophoretic devices may have cell densities from about 160 million cells/mL to about 670 million cells/mL, or from about 160 million cells/mL to about 320 million cells/mL, or from about 260 million cells/mL to about 535 million cells/mL, or from about 305 million cells/mL to about 670 million cells/mL, or from about 0.5 million cells/mL to about 5 million cells/mL.

The following examples are provided to illustrate the devices and processes of the present disclosure. The examples are merely illustrative and are not intended to limit the disclosure to the materials, conditions, or process parameters set forth therein.

Examples

The ability of an acoustophoretic system of the present disclosure to concentrate Jurkat T-cells was tested. Jurkat T-cells have a diameter of 11 micrometers (μm) to 14 μm. An acoustophoretic device was used, and a Beckman Coulter Vi-CELL X was used at various test conditions to measure the cell density reduction.

Figure 29:
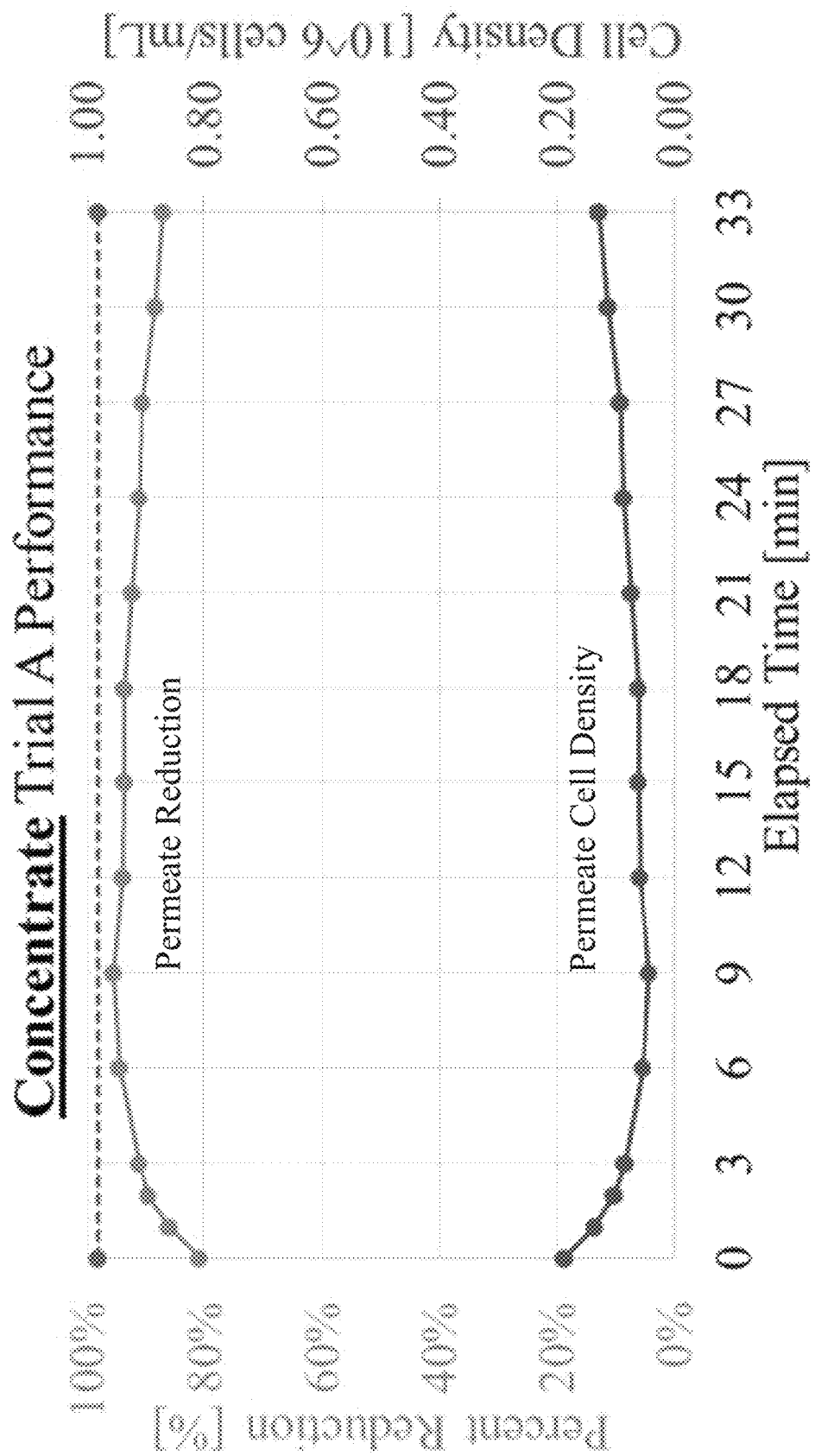
FIG. 29 is a two-axis graph showing the results of trial A. The left-hand y-axis is the percent reduction of cells in the permeate, and runs from 0 to 100% at intervals of 20%. The right-hand y-axis is the cell density of the permeate in units of million cells/mL, and runs from 0 to 1.00 at intervals of 0.20. The x-axis is elapsed time in minutes, and runs from 0 to 33 minutes at intervals of 3. The dotted line indicates the initial cell density, which was 0.98 million cells/mL.

In the first trial A, the T-cells were concentrated, and the cell density of the permeate was measured. The dotted line indicates the feed cell density. Desirably, the cell density in the permeate is as low as possible, indicating that the cells are retained in the concentrate. The graph in FIG. 29 shows the results of trial A over time. The results show very low cell densities in the permeate, between 0.0 and 0.2 million cells/mL, showing that most of the cells are in the concentrate. The results also show a high permeate reduction percentage, between 80% and 99%.

Figure 30:
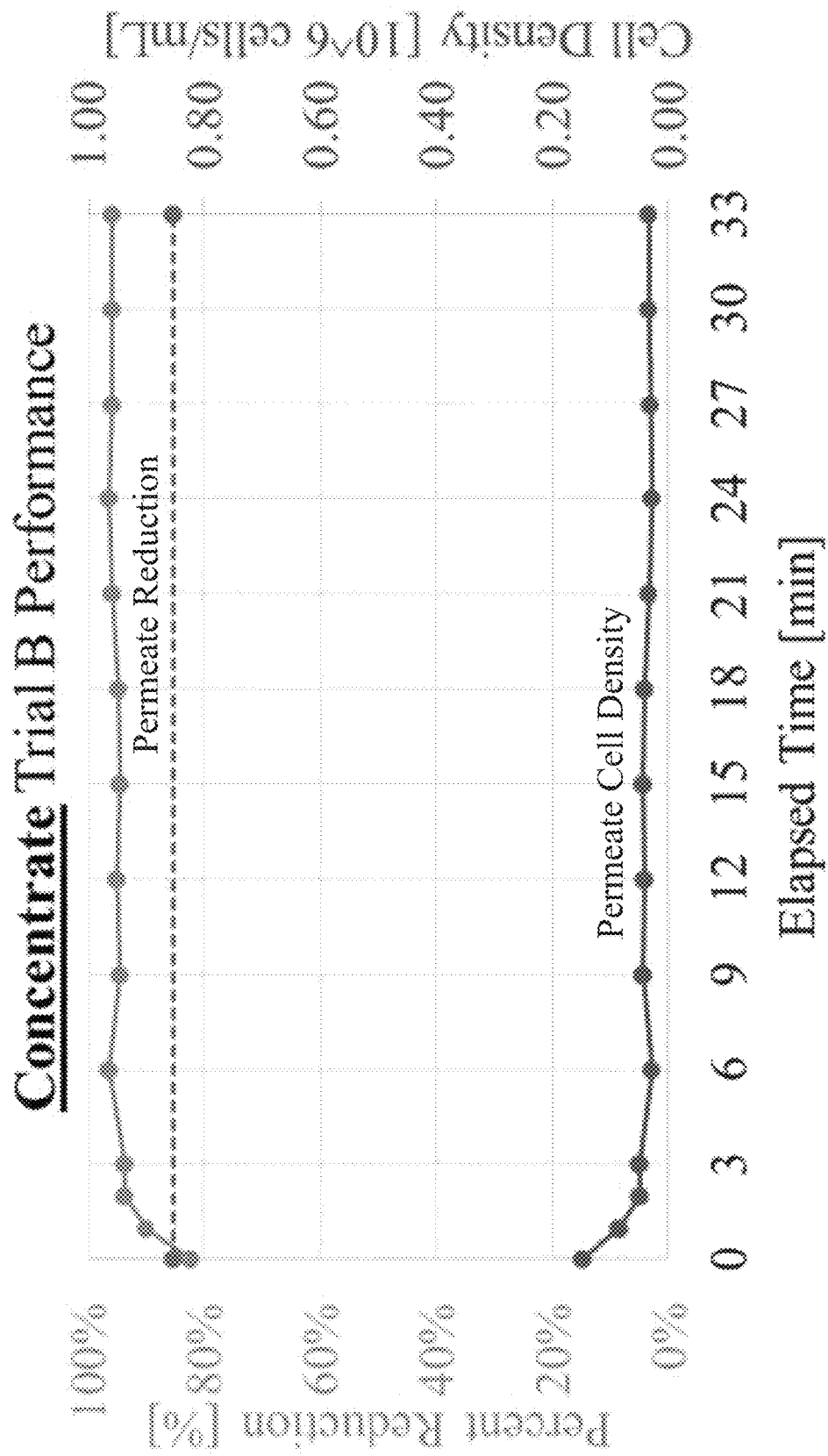
FIG. 30 is a two-axis graph showing the results of trial B. The left-hand y-axis is the percent reduction of cells in the permeate, and runs from 0 to 100% at intervals of 20%. The right-hand y-axis is the cell density of the permeate in units of million cells/mL, and runs from 0 to 1.00 at intervals of 0.20. The x-axis is elapsed time in minutes, and runs from 0 to 33 minutes at intervals of 3. The dotted line indicates the initial cell density, which was 0.85 million cells/mL.

In the second trial B, the T-cells were concentrated, and the cell density of the permeate was measured. The dotted line indicates the feed cell density. FIG. 30 shows the results over time. The results show good performance, with the permeate cell density being below 0.1 million cells/mL after minute 1, and greater than 95% permeate reduction after minute 2.

Figure 31:
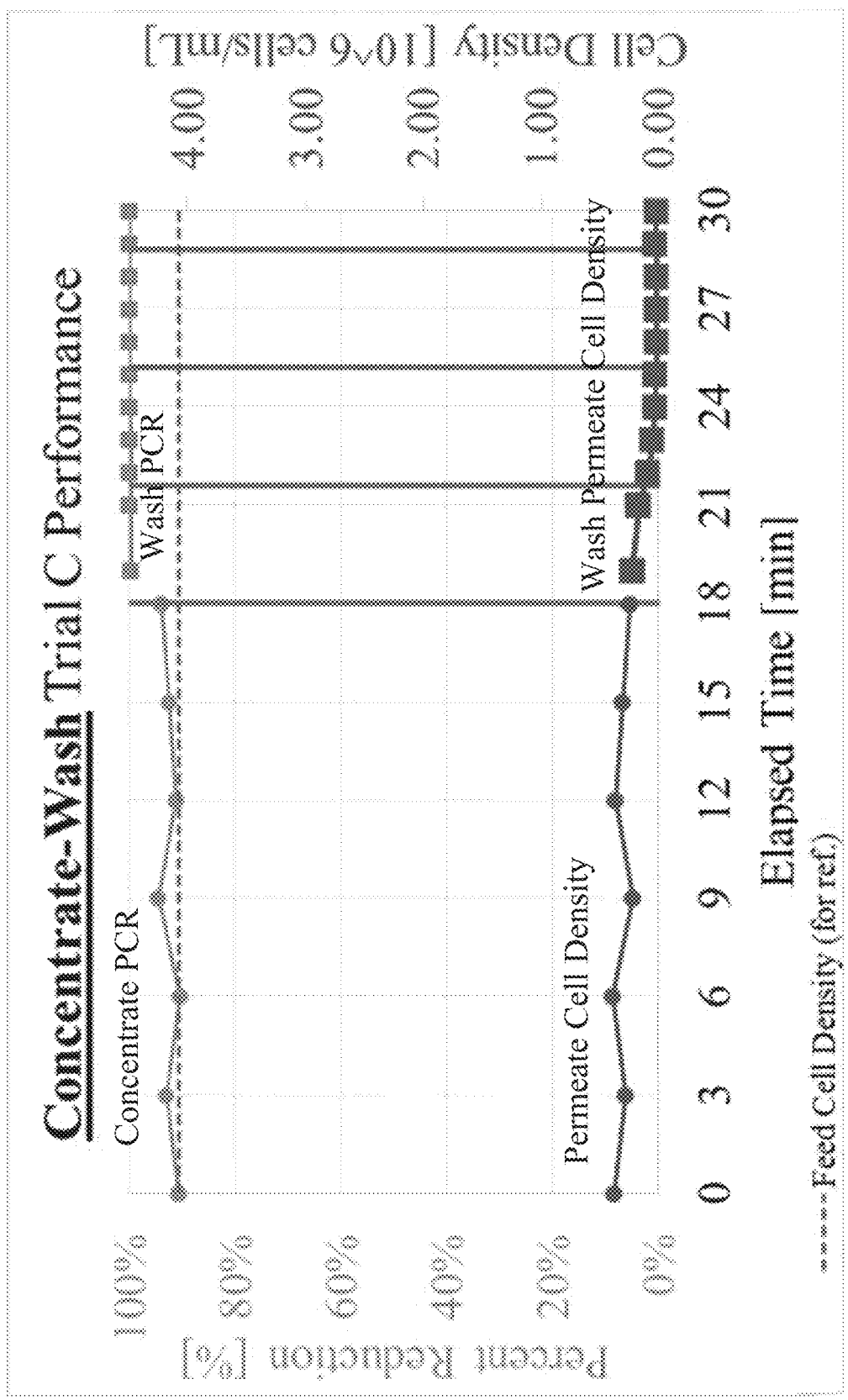
FIG. 31 is a two-axis graph showing the results of trial C. The left-hand y-axis is the percent reduction of cells, and runs from 0 to 100% at intervals of 20%. The right-hand y-axis is the cell density in units of million cells/mL, and runs from 0 to 4.00 at intervals of 1.00. The x-axis is elapsed time in minutes, and runs from 0 to 30 minutes at intervals of 3. The dotted line indicates the initial cell density, which was 4.08 million cells/mL.

In the third trial C, the T-cells were concentrated and washed. The concentrating occurred for the first 18 minutes, and washing was subsequently performed. FIG. 31 shows the results over time. The dotted line indicates the feed cell density. The solid vertical lines indicate when concentrated system volumes were processed (three total volumes were processed). Note that this graph includes data on the concentrate and the permeate (not just the permeate). All of the cells obtained from concentration were maintained through washing, e.g., concentrated cells were not lost due to the addition of the washing process. The table below provides additional information on these three trials. Retention and recovery rates of greater than 90% were obtainable for Jurkat T-cells.

| Trial | Feed Volume (mL) | Feed Density (cells/mL) | Concentrate Volume | Cell Recovery | Concentration Factor | Process Time (min) |
|---|---|---|---|---|---|---|
| A | 997 | 0.98 × 10$^6$ | 21 mL | 91% | 47X | 33 |
| B | 1004 | 0.85 × 10$^6$ | 21 mL | 95% | 48X | 33 |
| C | 555 | 4.08 × 10$^6$ | 20 mL | 92% | 28X | 31 |

The liquid volumes used to completely wash the concentrated cells were tracked. Tracking the liquid volumes can be useful in applications such as, for example, removing electroporation buffer from a cell culture prior to transduction or transfection of the cell culture.

Figure 32:
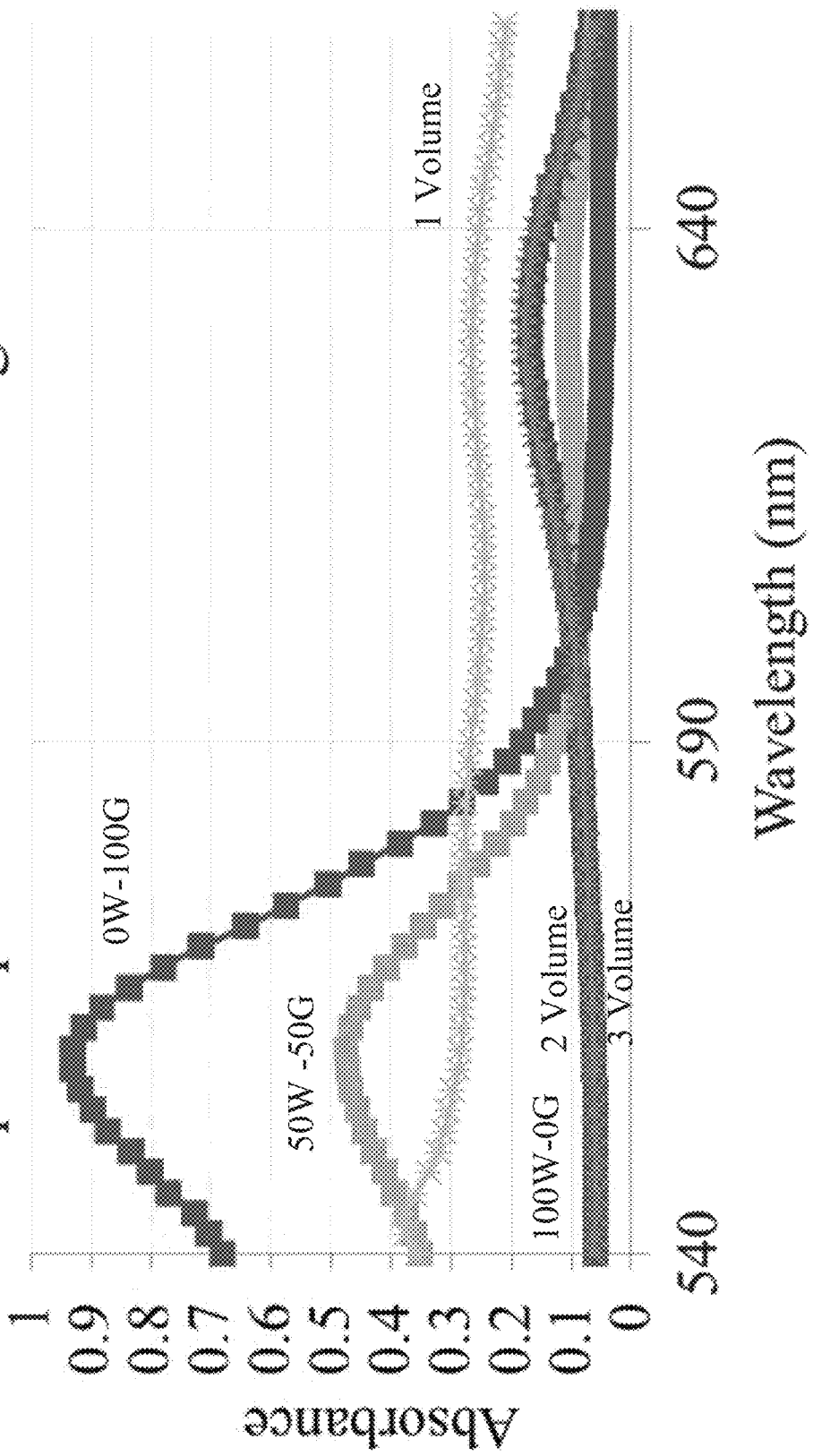
FIG. 32 is a graph showing the absorbance at different wavelengths for six different samples. Those samples are: 100% wash media (100W-0G), 50% wash media and 50% growth media (50W-50G), 100% growth media (0W-100G), first volume of the wash (1 Volume), second volume of the wash (2 Volume), and third volume of the wash (3 Volume). The y-axis is absorbance, and runs from 0 to 1 at intervals of 0.1. The x-axis is wavelength, and runs from 540 nm to 640 nm at intervals of 50 nm.

A blue wash media and a red growth media were used. A Molecular Devices SpectraMax spectrophotometer was used to measure the two different wavelengths of these two media to identify a complete flush/washing out of the old growth media from the system. Three samples were measured: 100% wash media (100W-0G), 50% wash media and 50% growth media (50W-50G), and 100% growth media (0W-100G). Three samples of the actual process were then tested (1 Volume, 2 Volume, 3 Volume). As seen in the spectrophotometer results shown in FIG. 32, the second and third volumes fall on top of the 100% wash media curve (100W-0G), indicating that all of the growth media has been washed from the concentrated cells after 2 or 3 volumes have been used for washing.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method of washing particles, the method comprising:
providing an initial mixture of a first media and particles to a chamber of an acoustophoretic device, the acoustophoretic device including at least one ultrasonic transducer that includes a piezoelectric material;
driving the at least one ultrasonic transducer to create an acoustic wave in the chamber;
providing the initial mixture to the acoustic wave in a first direction, such that at least a portion of the particles are trapped and held against fluid flow in the acoustic wave;
forming clusters of the trapped particles to grow in size to exit the acoustic wave in a second direction that is different than the first direction; and
flowing a second media to the chamber while the particles and clusters are retained in the chamber to wash the first media out of the chamber.

2. The method of claim 1, wherein the second media is a biocompatible wash or a buffer solution.

3. The method of claim 1, wherein the particles are cells.

4. The method of claim 1, wherein the particles are microcarrier/cell complexes.

5. The method of claim 1, wherein the initial mixture has a density of about 0.5 million particles/ml to about 5 million particles/ml.

6. The method of claim 1, further comprising concentrating the particles in the initial mixture.

7. The method of claim 6, further comprising concentrating the particles to a concentrate volume that is about 25 to about 50 times less than a volume of the initial mixture.

8. The method of claim 7, further comprising concentrating the particles in the initial mixture to a concentrated particle density of about 25 to about 50 times greater than a particle density of the initial mixture.

9. The method of claim 1, wherein a cell density of a wash output of the chamber is about 0.0 to about 0.5 million cells/ml.

10. The method of claim 9, wherein the wash output is from a concentrate process and a wash process.

11. The method of claim 1, further comprising conducting a spectrophotometer process on the chamber to determine wash efficacy.

12. The method of claim 1, further comprising retaining 80 percent or more of the particles with the acoustophoretic device.

13. The method of claim 1, further comprising retaining or recovering at least 90% of the particles.

14. A method of recovering cells from a cell culture, comprising:
   feeding an initial mixture of the cell culture to a flow chamber of an acoustophoretic device, the acoustophoretic device including at least one ultrasonic transducer that includes a piezoelectric material that is configured to be driven to generate a multi-dimensional acoustic wave in the flow chamber; and
   driving the at least one ultrasonic transducer to generate a multi-dimensional acoustic wave in the flow chamber;
   providing the initial mixture to the multi-dimensional acoustic wave in a first direction; and
   retaining the cells from the initial mixture in the multi-dimensional acoustic wave to form clusters of the cells to grow in size to exit the multi-dimensional acoustic wave in a second direction that is different from the first direction to concentrate the cells.

15. The method of claim 14, wherein the cell density of the concentrated cells is about 25 to about 50 times greater than the cell density of the initial mixture.

16. The method of claim 14, wherein a volume of the concentrated cells is 25 to about 50 times less than a volume of the initial mixture.

17. The method of claim 14, wherein the concentrated cells are obtained in about 35 minutes or less.

18. The method of claim 14, further comprising washing the concentrated cells, wherein a cell density of a wash output of the flow chamber is about 0.0 to about 0.5 million cells/ml.

19. The method of claim 14, further comprising retaining 80 percent or more of the cells with acoustophoretic device.

20. The method of claim 14, further comprising retaining or recovering at least 90% of the cells.

21. An acoustophoretic device, comprising:
   a flow chamber;
   at least one ultrasonic transducer coupled to the flow chamber and including a piezoelectric material that is adapted to be driven to generate an acoustic wave in an acoustic region of the flow chamber, such that particle clusters form in the acoustic region that can grow in size to exit the acoustic region when a fluid and particle mixture is provided to the acoustic region;
   a collection region on an opposite side of the flow chamber from the acoustic region and being configured to collect particle clusters that exit the acoustic region; and
   a fluid input region between the acoustic region and the collection region that permits fluid flow into the acoustic region from a direction of the collection region, and permits particle clusters to pass from the acoustic region to the collection region, such that fluid flow and particle cluster flow are in opposite directions.

22. The acoustophoretic device of claim 21, wherein the flow chamber can contain a cell capacity of about 4 billion to about 40 billion cells.

* * * * *

UNITED STATES PATENT AND TRADEMARK OFFICE
CERTIFICATE OF CORRECTION

Page 1 of 1

PATENT NO. : 11,085,035 B2
APPLICATION NO. : 15/942427
DATED : August 10, 2021
INVENTOR(S) : Bart Lipkens et al.

It is certified that error appears in the above-identified patent and that said Letters Patent is hereby corrected as shown below:

On the Title Page

Line 9, in Inventors, item (72) delete "Simbsbury" and insert -- Simsbury --

Line 11, in Inventors, item (72) delete "Fast" and insert -- East --

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*